United States Patent
Davis et al.

(10) Patent No.: US 9,067,851 B2
(45) Date of Patent: Jun. 30, 2015

(54) SELECTIVE HYDROGENATION OF ALKYNYL-CONTAINING COMPOUNDS

(75) Inventors: S. Mark Davis, Humble, TX (US); Neeraj Sangar, League City, TX (US); Paul F. Keusenkothen, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 30 days.

(21) Appl. No.: 13/571,146

(22) Filed: Aug. 9, 2012

(65) Prior Publication Data

US 2013/0204056 A1  Aug. 8, 2013

Related U.S. Application Data

(60) Provisional application No. 61/527,379, filed on Aug. 25, 2011.

(30) Foreign Application Priority Data

Oct. 10, 2011 (EP) .................................. 11184555

(51) Int. Cl.
| | |
|---|---|
| C07C 4/02 | (2006.01) |
| C07C 11/00 | (2006.01) |
| C07C 2/76 | (2006.01) |
| C07C 2/02 | (2006.01) |
| C07C 5/09 | (2006.01) |

(52) U.S. Cl.
CPC ........................................ *C07C 5/09* (2013.01)

(58) Field of Classification Search
USPC ..................................................... 585/259, 500
See application file for complete search history.

(56) References Cited

U.S. PATENT DOCUMENTS

| | | | |
|---|---|---|---|
| 4,705,906 A | 11/1987 | Brophy et al. | |
| 4,906,800 A | 3/1990 | Henry et al. | |
| 7,045,670 B2* | 5/2006 | Johnson et al. | 585/259 |
| 7,153,807 B2* | 12/2006 | Molinier et al. | 502/177 |
| 7,404,936 B2* | 7/2008 | Mazanec et al. | 422/198 |
| 2009/0326288 A1* | 12/2009 | Mamadov et al. | 585/259 |

FOREIGN PATENT DOCUMENTS

| | | |
|---|---|---|
| DE | 198 04 806 | 8/1999 |
| WO | WO 2010/069543 | 6/2010 |

OTHER PUBLICATIONS

Assael et al., Measurement of the thermal conductivity of stainless steel AISI 340L up to 550 K, 2003, International journal of thermophysics, vol. 24, 4, pp. 1145-1153.*

* cited by examiner

*Primary Examiner* — In Suk Bullock
*Assistant Examiner* — Youngsul Jeong

(57) ABSTRACT

A selective hydrogenation method is particularly effective in selectively hydrogenating alkynyl compounds, such as acetylene or methyl acetylene, over alkenyl compounds, such as ethylene. The method produces a relatively high quantity of heat during the selective hydrogenation reaction. This production of heat is, however, quite beneficial in that enough heat is produced such that a substantial portion of the produced heat can be recovered for heat efficiency purposes.

8 Claims, 4 Drawing Sheets

SELECTIVE HYDROGENATION OF ALKYNYL-CONTAINING COMPOUNDS

PRIORITY

This application claims priority to Provisional Application No. 61/527,379 (2011EM224) filed on Aug. 25, 2011 and EP Application No. 11184555.8 filed on Oct. 10, 2011, the disclosures of which are incorporated herein by reference in their entireties.

FIELD

The present techniques relate to a process for selectively hydrogenating an alkyne to an alkene. More specifically, the present techniques relate to a process for selectively hydrogenating an alkyne to an alkene and at a conversion rate that provides recoverable heat to enhance the efficiency of the process.

BACKGROUND

Light olefin products (e.g., ethylene, propylene, and butene) generated by various technologies, such as gas to olefins, methanol to olefins, steam cracking or fluid catalytic cracking contain highly unsaturated byproducts, such as alkynes and alkadienes. These byproducts are subsequently removed from light olefins, because they can be poisons to downstream olefin polymerization catalysts.

One process for removing (via conversion) unsaturated byproducts, such as alkynes, such as acetylene and methyl acetylene, and alkadienes, such as propadiene and butadiene, from light olefin streams is selective hydrogenation. Selective hydrogenation is used to partially saturate the alkynes and butadienes to form the desired olefins. This process has been carried out using a variety of catalysts. Examples of selective hydrogenation catalysts include nickel or palladium and their alloys supported on alumina.

To perform the selective hydrogenation, four unit types are typically used: (i) front-end selective catalytic hydrogenation converters, (ii) back-end selective catalytic hydrogenation converters, (iii) methyl acetylene/propadiene (MAPD) selective catalytic hydrogenation converters and (iv) butadiene (BD) selective catalytic hydrogenation converters. These converters typically involve different feeds based on the specific process.

Typical acetylene conversion processes utilize fixed bed tubular converters incorporating engineered catalyst structures to manage heat and mass transfer within the converter. The engineered catalyst particles may be impregnated with active catalyst to convert feeds (e.g., acetylene) into products (e.g., ethylene). These processes tend to be utilized with lower temperature pyrolysis processes, such as steam cracking, which produce ethylene along with other lower amounts of byproducts, such as acetylene. As an example, the acetylene processed in a steam cracking process is typically less than (<) 2 mole percent (mol %) and more typically <0.3 mol %.

With higher acetylene concentrations, U.S. Pat. No. 4,705,906, describes a process that utilizes greater than (>) 1 mol % carbon monoxide in its process. The catalyst comprises a metal oxide or sulfide or mixture of metal oxides or sulfides having hydrogenation activity, for example ZnO either alone or in combination with other metal oxides or sulfides. As other examples, U.S. Pat. No. 7,153,807 discloses a selective hydrogenation process that uses non-palladium catalyst as the selective hydrogenation catalyst.

As an enhancement to the process, additional equipment has been proposed for hydrogenating hydrocarbons, such as a microchannel converter. As an example, U.S. Pat. No. 7,404,936 discloses that microchannel converters can be used in a variety of chemical reactions including hydrogenation. Palladium is given as one of many types of catalysts that can be used in the process.

Despite a long history of improvements to the selective hydrogenation processes and systems that can be used in the hydrogenation of hydrocarbons, additional problems remain. Such problems include the production of significant amounts of undesirable compounds, such as saturates (e.g., ethane, propane, butane), as well as the production of green oil ($C_4^+$ oligomer compounds). These saturates are typically formed due to over-hydrogenation of the alkynes and/or alkadienes and the non-selective hydrogenation of olefins. Green oil is generally formed as a result of oligomerization of the alkynes and/or alkadienes and/or olefins. Both saturates and green oil are undesirable due to a loss of the desired mono-olefins component of the product stream. Green oil is additionally troublesome in that it further decreases catalyst life by depositing heavy compounds on the catalyst surface.

In addition, other limitations are associated with the removal of heat and recovery of usable heat from the exothermic reactions in hydrogenation. For instance, as the process involves exothermic reactions, the process may lose control of the reactions (e.g., temperature control) if the temperature within the unit is not properly managed. For streams with low levels of acetylene (e.g., <2 mol %), the reactions may be managed selectively using conventional techniques because of the lower catalyst activity. However, for streams containing higher levels of acetylene (e.g., ≥2 mol %), conventional processes have problems controlling the reaction temperatures, while still remaining highly selective. In addition, the conventional processes are limited by heat and/or mass transfer. As a result, the catalyst has to be configured with low metal loadings to lower catalytic activity, may utilize readily accessible surface area and may include catalyst inhibitors (e.g., carbon monoxide). That is, as the process does not efficiently remove heat, the process has to limit reactions to prevent overheating of the unit. As such, the conventional processes are limited by heat generation and fail to effectively recover energy from the process.

As yet another problem, the selectivity is typically modest for vapor phase processes with a portion of the acetylene and/or ethylene converting to ethane and/or other undesired products. This low selectivity may not be problematic for lower temperature conversion processes (e.g., steam cracking), which involve streams having a relatively low acetylene content. However, for higher acetylene content streams, the lower selectivity results in recycles and/or multiple conversion stages. These inefficiencies increase the cost and size of equipment and operations and add undesired complexity to the system.

Accordingly, enhancements in selective hydrogenation processes are desired to increase the hydrogenation of alkynyl-containing compounds and polyunsaturated compounds over hydrogenation of mono-unsaturated compounds. Enhancements in selective hydrogenation processes are also desired to enhance efficiency in the process, such as increasing heat recovery from reactions in the process and increasing feed conversion rates. Further, it may also be desirable to integrate the hydrogenation process with the conversion of hydrocarbons to provide additional efficiencies for the system.

SUMMARY OF THE INVENTION

The present techniques provide a selective hydrogenation process using a microchannel converter that is particularly effective in selectively hydrogenating alkynyl compounds, such as acetylene or methyl acetylene, over alkenyl compounds, such as ethylene. The selective hydrogenation process may also be effective in lessening green oil formation. The selective hydrogenation process of the present techniques can be operated at temperatures enabling efficient heat recovery based on the operation of the microchannel converter. This recovered heat may be integrated to preheat one or more feeds to one or more reactors, utilized to preheat a fluid provided as a diluent, or utilized in other processes that enhance the efficiency of the system. Additionally, this process also enables a high feed conversion rate relative to the catalyst volume used in the converter, meaning that less total catalyst volume can be used relative to conventional selective hydrogenation systems. That is, the microchannel converters can provide a unit that lessens the footprint utilized within the plant, while enhancing the operation of the system as compared to conventional systems. The selective hydrogenation process is carried out so that the heat is transferred effectively from the alkenyl product to a heat transfer fluid to minimize catalyst deactivation or lower selectivity. The process is particularly well suited for feed streams containing higher acetylene concentrations (e.g., >2 mol %) that can be produced using high severity pyrolysis methods.

According to one aspect of the present techniques, there is provided a method for selectively hydrogenating an alkyne. The method comprising: flowing a feed stream comprising molecular hydrogen and greater than or equal to 2 mol % alkyne through at least one conduit containing a hydrogenation catalyst (e.g., a selective hydrogenation catalyst); contacting the feed stream with the hydrogenation catalyst to produce an alkene-containing product stream at operating conditions sufficient to yield an alkyne to an alkene conversion rate of at least 0.4 moles/hour/cc of hydrogenation catalyst and to produce heat; and recovering at least a portion of the heat through heat exchange with a heat transfer fluid. The heat is produced in the method at operating conditions sufficient to yield a catalyst heat release rate $\geq 1.8$ MJ/hr/cc of hydrogenation catalyst. The feed stream may include at least 2 mol % alkyne based on the feed stream or at least 5 mol % alkyne based on the feed stream.

The method may include different techniques to recover and utilize the heat. For instance, recovering the heat may include passing the heat transfer fluid through at least one of a plurality of conduits in the microchannel converter, heating the heat transfer fluid via indirect heat transfer and removing the heat transfer fluid from the microchannel converter. This recovery of heat may be via indirect heat exchange through a material having a thermal conductivity of $\geq 10$ W/m-C. The method of claim 1, wherein the hydrogenation catalyst is disposed on an inner wall of the conduit.

The conversion of the alkyne to alkene is carried out in the conduit. The hydrogenation catalyst may have an alkyne conversion $\geq 80\%$ at operating conditions, selectivity to alkene $\geq 50$ mol % at operating conditions, and selectivity to green oil of $\leq 10$ weight percent (wt %) at operating conditions. The hydrogenation catalyst may include greater than or equal to 2 wt % of a metal selected from Groups 8 to 10 of the Periodic Table based on the total weight of the hydrogenation catalyst. In particular, the hydrogenation catalyst may comprise >0.5 wt % palladium and/or platinum. In addition, the hydrogenation catalyst may include >0.01 wt % of one or more promoter elements selected from Groups 1, 2, 11, 12, 13, and 14 of the Periodic Table based on the total weight of the hydrogenation catalyst.

The method may utilize at least a portion of the extracted heat to reduce energy consumption in the process. The extracted heat may be utilized to (i) generating steam from the heat transfer fluid, (ii) converting the heat transfer fluid into energy, (iii) combining the heat transfer fluid with a hydrocarbon containing feed provided to a conversion reactor upstream of the flowing, wherein the feed stream is derived from effluent from the conversion reactor, and/or (iv) heating conversion reactor feed (e.g., one of reactants or pyrolysis feed) via the heat transfer fluid. In particular, the extracted heat is utilized to reduce conversion reactor feed utilized in a conversion reactor, wherein the feed stream is derived from effluent from the conversion reactor. The heat transfer fluid may be one or more of water and steam.

In one or more embodiments, the method may include passing an oxidant containing stream and a fuel containing stream to a conversion reactor during a heating step; and passing one of the oxidant containing stream and the fuel containing stream through a microchannel converter; reacting the oxidant containing stream and the fuel containing stream to form combustion products and combustion heat within the conversion reactor; removing the combustion products from the conversion reactor; passing the pyrolysis feed to the conversion reactor; and exposing the pyrolysis feed to the combustion heat within the conversion reactor to produce the reactor product comprising acetylene, wherein at least a portion of the reactor product is the feed stream. The exposing a pyrolysis feed to a peak pyrolysis gas temperature $\geq 1500.0°$ C. within the conversion reactor, which is a regenerative reverse flow reactor.

In yet another embodiment, a system for processing hydrocarbons to produce ethylene is described. The system may include a conversion reactor and a microchannel reactor. The conversion reactor may be configured to convert a hydrocarbon containing feed into a feed stream containing acetylene. The microchannel converter may be in fluid communication with the conversion reactor and configured to convert a portion of the acetylene from the feed stream into ethylene and having: a plurality of process flow conduits, wherein at least one of the plurality of process flow conduits have a hydrogenation catalyst disposed on an interior surface and permit flow of the feed stream through the process flow conduit; and a plurality of heat exchange conduits, wherein the plurality of heat exchange conduits are configured to pass a heat exchange fluid through the plurality of heat exchange conduits to recover at least a portion of the heat through heat exchange with the heat transfer fluid. In this system, the microchannel converter may be directly coupled to the conversion reactor and/or integrated with the conversion reactor.

In one or more embodiments, the conversion reactor, which may be a regenerative reverse flow reactor, may include different equipment. For instance, the conversion reactor may include one or more reactor beds and the microchannel converter is disposed adjacent to at least one of the one or more reactor beds. The conversion reactor may also include one or more poppet valves disposed between at least one of the one or more reactor beds and the microchannel converter. The reactor may include a reactor body, wherein the reactor body forms a reaction region within the reactor body; and one or more valve assemblies coupled to the reactor body and in flow communication with the reaction region and configured to control fluid flow of the at least a portion of the hydrocarbon containing feed between a location external to the reactor body and within the reaction region.

In one or more embodiments, the microchannel converter may include different configurations. For instance, the at least one of the plurality of process flow conduits may have a cross sectional area of less than or equal to 50 mm$^2$ and the plurality of process flow conduits may be formed from a material having a thermal conductivity of ≥10 W/m-C.

The system may also include other equipment. For instance, one or more conduits may be configured to transport a heat transfer fluid to the microchannel converter and pass the heat transfer fluid from the microchannel converter to a heat exchanger upstream of the conversion reactor. In another embodiment, the one or more conduits may be configured to transport a heat transfer fluid to the microchannel converter and pass the heat transfer fluid from the microchannel converter to a steam turbine.

Figure 1:
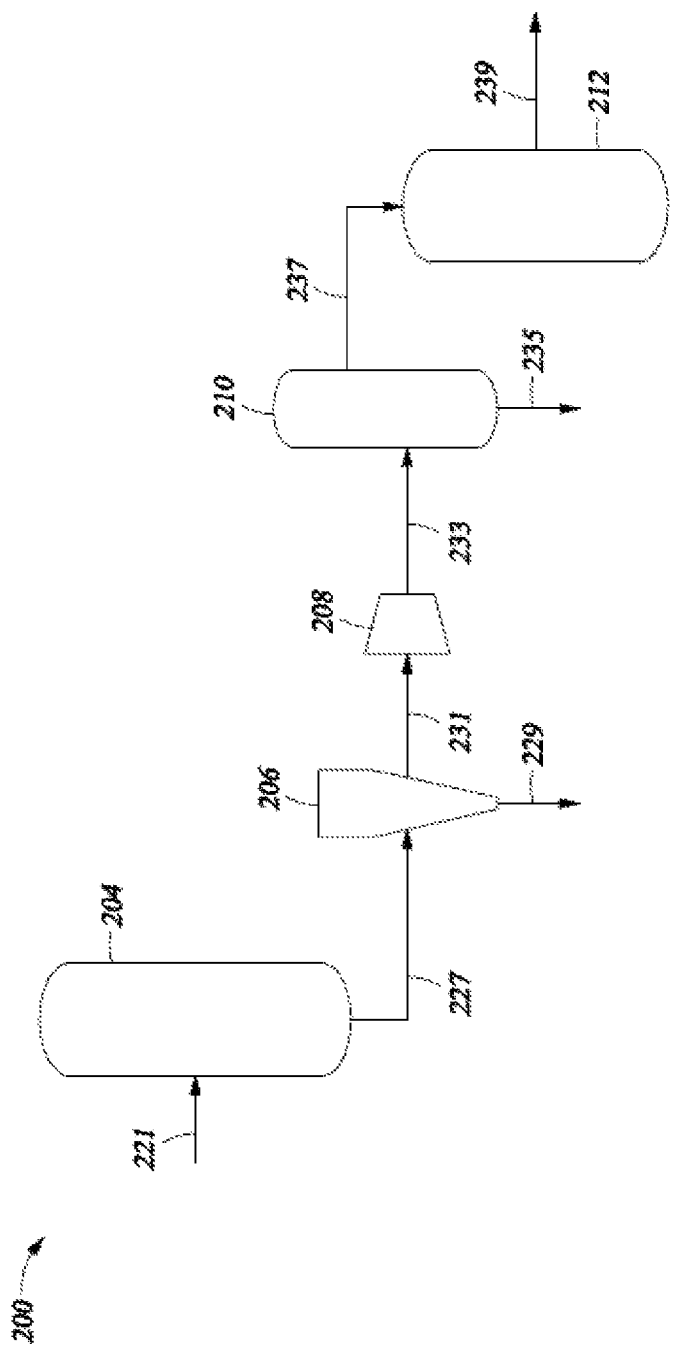
FIG. 1 is a simplified diagrammatic illustration of an exemplary process for converting a feed into conversion products in accordance with an embodiment of the present techniques.

Although the present techniques can be described in terms of a hydrogenation process for producing ethylene, the invention is not limited thereto. In other words, to the extent that the following detailed description is specific to a particular embodiment or a particular use, this is intended to be illustrative only, and is not to be construed as limiting the scope of the invention. On the contrary, it is intended to cover all alternatives, modifications and equivalents that may be included within the spirit and scope of the invention, as defined by the appended claims.

DETAILED DESCRIPTION OF THE INVENTION

I. Selectively Hydrogenating Acetylene

The present techniques provide a process for selectively hydrogenating alkynyl compounds. Selective hydrogenation refers to the hydrogenation of alkynyl compounds to produce a product comprised of predominantly alkenyl compounds. The process is particularly effective in the selective hydrogenation of acetylene to produce predominantly ethylene from the converted acetylene. Although some alkyl compounds may be formed such as ethane, selective hydrogenation favors the formation of alkenyl compounds.

The process of the present techniques produces a relatively high quantity of heat during the selective hydrogenation reaction. This production of heat is, however, quite beneficial in that enough heat is produced such that a substantial portion of the produced heat can be recovered for energy efficiency purposes, while lessening catalyst deactivation due to the high heat release during the conversion of the alkynyl compounds to the alkenyl compounds. A particularly efficient means of capturing the heat is through the production of steam, such as producing steam at a pressure of at least 100 pounds per square inch gauge (psig) (689 kilo Pascals (kPa)) or at least 200 psig (1379 kPa). The steam can be used for various purposes, such as the working fluid for steam turbine machinery or compressors, as a co-feed into catalytic conversion processes, or as a diluent and/or heat transfer medium into thermal cracking processes.

II. Selective Hydrogenation Catalyst

The catalyst composition used according to the present technique is capable of hydrogenating alkynes. Examples of such alkynes include $C_2$ to $C_4$ alkynes, such as acetylenic compounds (e.g., acetylene and methyl acetylene). The alkynes can be included in a feed stream that also contains other compounds such as olefins, and in such a case, the catalyst has high selectivity to olefins and low selectivity to green oil (e.g., oligomers formed from two or more alkyne or olefin molecules) and saturates.

In one embodiment, the selectivity ratio may be defined as a molar ratio of alkenes to converted alkynes for the process. For instance, the acetylene hydrogenation selectivity is the molar ratio of the acetylene converted to ethylene over the total amount of acetylene converted. If this ratio is below 0.5, then the catalytic material has low selectivity. For selectivity ratios greater than or equal to (≥) 0.5, the catalytic material has high selectivity. Accordingly, in certain embodiments, the high selectivity includes a selectivity ratio ≥0.5, ≥0.6, or ≥0.8.

In another embodiment, when used to selectively hydrogenate one or more of $C_2$ to $C_4$ alkynes in a feed stream that may also contain one or more of $C_2$ to $C_4$ olefins, the selective hydrogenation catalyst can achieve an alkyne conversion ≥80 mol %, such as ≥90 mol %, with a selectivity to alkene ≥50 mol %, such as ≥60 mol % or ≥70 mol %, and a selectivity to green oil of less than or equal to (≤) 10 wt %, such as ≤8 wt % or ≤4 wt %. The reduction in green oil formation should also result in an extension of catalyst lifetime and/or operating cycle.

The catalyst composition contains at least one metal from Groups 8 to 10 of the Periodic Table of the Elements. The Periodic Table of Elements referred to herein is the IUPAC version described in the *CRC Handbook of Chemistry and Physics,* 78th Edition, CRC Press, Boca Raton, Fla. (1997). Examples of metals from Group 8 include iron, ruthenium and osmium, with iron and ruthenium being preferred metals. Examples of metals from Group 9 include cobalt, rhodium and iridium, with rhodium being a preferred metal. Examples of metals from Group 10 include nickel, palladium and platinum, with palladium and platinum being preferred metals, and palladium being more preferred.

In certain embodiments, the catalyst composition contains a quantity of elements from at least one of the metals selected from the Groups 8 to 10 of the Periodic Table to convert alkyne to alkene at operating conditions sufficient to yield a conversion rate of at least 0.4 moles/hour/cc hydrogenation catalyst. Preferably, the catalyst composition contains a quantity of elements from at least one of the metals selected from the Groups 8 to 10 of the Periodic Table to convert alkyne to alkene at operating conditions sufficient to yield a conversion rate of ≥1 moles/hour/cubic centimeter (cc) of hydrogenation catalyst, alternatively ≥5 moles/hour/cc of hydrogenation catalyst, alternatively ≥10 moles/hour/cc of hydrogenation catalyst, alternatively ≥20 moles/hour/cc of hydrogenation catalyst. Generally, the catalyst composition should contain a quantity of at least one of the Groups 8 to 10 metals to convert alkyne to alkene at operating conditions sufficient to yield a conversion rate of up to and including 25 moles/hour/cc of hydrogenation catalyst (e.g., ≤25 moles/hour/cc of hydrogenation catalyst).

In an embodiment, the selective hydrogenation catalyst comprises ≥0.3 wt % metal selected from the Groups 8 to 10 of the Periodic Table, based on the total catalyst composition.

The selective hydrogenation catalyst can comprise ≥0.3 wt %, ≥1 wt %, or ≥2 wt %, or ≥4 wt %, or ≥5 wt % metal selected from the Groups 8 to 10 of the Periodic Table, based on the total catalyst composition. Generally, the catalyst composition contains up to and including 10 wt % metals selected from the Groups 8 to 10 of the Periodic Table, based on the total catalyst composition. The catalyst may include ≥0.5 wt % palladium or platinum based on the total catalyst composition.

The catalyst may also contain other promoters or modifiers that are used to further improve selectivity for selective alkyne hydrogenations. Examples include Group 11 to 14 elements, such as copper, silver, zinc, tin, and gallium and/or alkali or alkali earth additives from Groups 1 and 2. In a preferred embodiment, the additional components or promoters are used to improve activity or selectivity for selective hydrogenation of alkynes to alkenes as compared to the unmodified catalyst. Alternative modifiers include other Group 11 to 14 elements, such as gold or indium, alone or in combination, or in combination together with one or more alkali or alkali earth additives such as potassium, magnesium, calcium, etc. The catalyst may comprise >0.01 wt % of one or more promoter elements selected from Groups 1, 2, 11, 12, 13, and 14 of the Periodic Table based on the total weight of the catalyst. Alternatively, the catalyst may comprise about 0.1 wt % or more of modifier or promoter elements, and, generally, the atomic ratio of promoter elements to Group 11 to 14 metals are in the range of about 0.1 to 5, although lower or higher ratios can be utilized depending on specific cost and performance tradeoffs. These various combinations of promoters may include two, three or more different modifiers.

The catalyst composition may aid in the selective hydrogenation reactions that produce sufficient heat, such that at least a portion of that heat can be recovered for energy efficiency purposes. For example, the recovered heat may be utilized to generate steam that can be used as a heat source. According to the present techniques, the catalyst composition aids in the recovery of heat by having the ability to release heat produced in the selective hydrogenation reaction. Preferably, the heat produced in the hydrogenation reaction is produced at operating conditions sufficient to yield a catalyst heat release rate of at least 1.8 Mega Joules/hour/cubic centimeter (MJ/hr/cc) of hydrogenation catalyst. Alternatively, the heat produced in the hydrogenation reaction is produced at operating conditions sufficient to yield a catalyst heat release rate of at least 10 MJ/hr/cc hydrogenation catalyst or at least 50 MJ/hr/cc hydrogenation catalyst. Generally, the heat produced in the hydrogenation reaction should be produced at operating conditions sufficient to yield a catalyst heat release rate of up to and including 100 MJ/hr/cc of hydrogenation catalyst (e.g., ≤100 MJ/hr/cc of hydrogenation catalyst).

In addition to the one or more metal components and promoters discussed above, the catalyst composition generally includes a support or binder material. Suitable support materials include, but are not limited to, carbon, silicon nitride, silicon carbide, boron nitride, magnesium silicate, bentonite, zeolites, metal alloys, zirconia, alumina, silica, silica-alumina, ceria-alumina, aluminates (such as aluminates of Groups 1 and 2 of the Periodic Table of Elements), and magnesium oxide-silicon oxide mixtures. Preferred support materials include carbon, zirconia, alumina, and ceria-alumina. The binder or support material can comprise from 50 wt % to 99.4 wt %, alternatively from 65 wt % to 96 wt %, of the entire catalyst composition.

Depending on the specific catalyst system and target activity, the catalyst support can be beneficially formulated with highly open structures. For example, average micropore diameters above 10 nanometer (nm), or greater than 20 nm or even above 50 nm can be preferred to ensure the acetylene conversion rates are not limited by micropore diffusion or related mass transfer limitations.

The feed stream may also contain small levels of additional additives, such as carbon oxides, especially carbon monoxide. Depending on the specific catalyst and operating conditions, addition of carbon monoxide into the feed stream can be used to reduce formation of fully saturated hydrocarbons such as ethane. Carbon oxides are typically used at lower concentrations in the range of 0.1 mol % to 5 mol %, in the range of 0.1 mol % to 1 mol %, or in the range of 0.3 mol % to 0.9 mol % based on the feed gas mixture entering the selective hydrogenation unit. Additionally, other additives may include triphenylphosphine (TPP), as an example.

III. Selective Hydrogenation Converter and Process Conditions

The selective hydrogenation of the alkyne-containing feed stream is carried out by flowing a feed stream containing the alkyne through at least one conduit containing the selective hydrogenation catalyst in a hydrogenation converter. As the feed stream flows through the conduit, catalyst within the conduit acts to produce a product by selectively converting alkyne to alkene.

During the selective hydrogenation of the alkyne to alkene, heat is also produced. According to the present techniques, the selective hydrogenation reaction produces sufficient heat, such that at least a portion of that heat can be recovered for heat efficiency purposes, such as, for example, converting the recovered heat to steam that can be used as a heat source. The heat source may be used to preheat feed to a reactor and/or a diluent for the reactor or another unit, such as a steam cracking furnace. Conventional acetylene conversion processes can have a catalyst heat release rate of much less than 1.5 MJ/hr/cc hydrogenation catalyst. These processes utilize lower activity catalysts or low acetylene concentrations to manage the exothermic reactions and resulting produced heat. Further, these processes tend to reject heat to the environment without energy recovery.

According to the present techniques, the catalyst composition aids in the recovery of heat by having the ability to release a relatively high quantity of heat in the selective hydrogenation reaction in a smaller unit volume. Preferably, the heat produced in the hydrogenation reaction is produced at operating conditions sufficient to yield a catalyst heat release rate of at least 1.8 MJ/hr/cc hydrogenation catalyst along with the other ranges noted above.

Heat release from the selective hydrogenation of alkynyl compounds to alkenyl compounds can be controlled to lessen catalyst deactivation or loss of selectivity. For example, in one embodiment, the heat produced in the selective hydrogenation is produced at operating conditions sufficient to yield a catalyst heat release rate of ≤120 MJ/hr/cc hydrogenation catalyst. In an alternative embodiment, the heat produced in the selective hydrogenation is produced at operating conditions sufficient to yield a catalyst heat release rate of ≤115 MJ/hr/cc hydrogenation catalyst.

By operating in these ranges, the process operates at temperatures where heat may be recovered efficiently, but below the temperatures that hinder the ongoing operation of the process. Accordingly, suitable operating conditions may include different operating temperatures and operating pressures to be able to recover energy during steady-state operation. For instance, the process may include an average hydrogenation reaction temperature ≥125° C., ≥150° C., or ≥200° C., but ≤500° C., ≤400° C., or ≤300° C. In certain embodiments, the average reaction temperature may be in the range from 125° C. to 500° C.; alternatively, from 150° C. to 400° C., or 200° C. to 300° C. The average hydrogenation reaction temperature may be measured via thermocouples located within the microchannel converter unit and/or associated with the microchannel converter unit. The average hydrogenation reaction temperature may be the average over a period of time for one or more thermocouples during the steady state operation of the unit.

Operating pressures include an average reaction pressure of ≥50 psig (340 kPa), ≥100 psig (690 kPa), ≥103 psig (710 kPa), or ≥200 psig (1400 kPa), but may be ≤1000 psig (6900 kPa), ≤600 psig (4137 kPa), ≤500 psig (3900 kPa), or ≤440 psig (3400 kPa). Also, the average reaction pressure includes ranges from 50 psig to 1000 psig (340 kPa to 6900 kPa); alternatively, from 200 psig to 500 psig (1400 kPa to 3900 kPa), from 100 psig to 500 psig (690 kPa to 3900 kPa), from 100 psig to 600 psig (690 kPa to 4137 kPa); or alternatively, from 200 psig to 440 psig (1400 kPa to 3400 kPa).

The conduit should have a cross sectional area that provides for effective heat transport during the selective hydrogen process. The effective transport of heat means that heat produced can be efficiently transported away from the unit along with the product of the conversion of the alkyne so that at least a portion of the heat can be recovered for reuse. Preferably, the heat is recovered in the form of steam or other suitable fluid.

The conduit can be of any shape suitable to effectively flow the feed stream through the conduit. For example, the conduit can have a cross section in the form an oval, including a circle, or in the form of any typical multisided geometric form such as in the form of a triangle, hexagon, or rectangle, including a square. In an embodiment, the conduit has a cross sectional area of ≥1 squared millimeters ($mm^2$), or ≥2 $mm^2$, or ≥10 $mm^2$ The conduit preferably has a cross sectional area of ≤50 $mm^2$ or ≤40 $mm^2$. The cross sectional area as referred to herein is measured on the basis of the area of the conduit open to fluid flow and excluding catalyst.

Any hydrogenation converter that includes one or more of the desired conduits can be used. One example of such a converter is disclosed in U.S. Pat. No. 7,404,936, and is referred to as a microchannel converter.

Preferably, the length of the conduit containing the hydrogenation catalyst is ≥1 centimeter (cm), more preferably in the range from 1 to 40 inches (2.5 to 100 cm). Typically, the sides or surfaces of the conduit are defined by walls. These walls are preferably made of a hard material such as a ceramic or metal. More preferably, the walls are comprised of a relatively highly thermally conductive material.

A desirable hydrogenation converter preferably includes a plurality of conduits and/or a plurality of adjacent heat exchange conduits. The plurality of conduits may contain, for example 2, 10, 100, 1000 or more conduits. In some preferred embodiments, a plurality of conduits is arranged in parallel arrays of planar conduits. Layers of reaction conduits can be alternated with layers of heat exchange conduits or two layers of reaction conduits sandwiched between heat exchange conduits, etc. During operation, the heat exchange conduits contain flowing heating and/or cooling fluids, for example water. Flows between layers can be co-flow, counter-flow, cross-flow or a combination of lows (diagonal flow). Conduits within a single layer can be also co-flow or counter flow. Non-limiting examples of this type of converter are disclosed in U.S. Pat. Nos. 6,200,536, 6,192,596 and 6,129,973. Performance advantages in the use of this type of architecture for the purposes of the present techniques include relatively large heat and mass transfer rates, and the substantial absence of any explosive limits. Use of such multi-conduit converters can enhance temperature control, and maintain a relatively more isothermal profile (or, in some embodiments, a well-controlled temperature gradient), as compared to conventional converters.

In some embodiments, the reaction conduit (e.g., process flow conduit) contains a "bulk flow region" or an open flow path. The terms "open flow path" or "bulk flow region" refer to an unobstructed, contiguous bulk flow region within the reaction conduit. A contiguous bulk flow region allows rapid gas flow through the reaction conduit without large pressure drops. In preferred embodiments, there is laminar flow in the bulk flow region. Bulk flow regions within each reaction conduit preferably have a cross-sectional area of $5 \times 10^{-8}$ to $1 \times 10^{-2}$ $m^2$ (meters squared), more preferably $5 \times 10^{-7}$ to $1 \times 10^{-4}$ $m^2$. The bulk flow regions preferably comprise ≥5%, more preferably in the range of 30% to 80% of either: (i) the internal volume of the reaction conduit, or (ii) the cross-section of the reaction conduit. Flow patterns as well as flow rate can be tailored to achieve desired temperature gradients within the reaction conduits along the flow direction.

Heat transfer fluids that can be used in recovering heat from the selective hydrogenation reaction may include any known heat transfer fluids, such as water, aqueous solutions, silicone oils, molten salts, liquid metals, etc. In some preferred embodiments, the heat exchange fluid is steam or is a fluid that undergoes a phase change in the heat exchanger under the intended process temperatures.

In addition to the reaction conduits, additional features, such as heat exchangers, may be included as a part of the hydrogenation converter. Conduit-type heat exchangers (e.g., heat exchange conduits) are preferred. However, any type of heat exchanger may be attached to the converter conduit by appropriate piping and adapters. The heat exchangers can be integral to the converter (e.g., they can be formed as one continuous conduit-type unit within the converter). In some preferred embodiments, a feed stream is preheated by the heat exchanger, this preheated stream then flows into the converter conduit (e.g., heat exchange conduits). Alternatively, the hydrogenation product stream from the converter conduit can transfer heat to the feed stream. The heat exchanger can be incorporated into the converter conduit in the form of a preheat zone. Heat exchangers can exchange heat between the feed stream and a separate, hot or cold heat exchange fluid stream (typically the streams are separated by a wall or walls of a multi-channel hydrogenation converter), or they can exchange heat between the inlet and outlet streams of the hydrogenation converter, or both. In some embodiments, the converter is configured to send the product stream into a second converter containing the reaction conduit or a plurality of reaction conduits or recycle the hydrogenation product stream back into the same converter containing the converter conduit or conduits. Heat exchange fluid can be gas or liquid and may include steam, liquid metals, or any effective heat exchange fluid. The system can be configured to include a phase change in the heat exchanger portion. In an embodiment, multiple heat exchange layers are interleaved with multiple reaction conduits (for example, at least 10 heat exchangers interleaved with at least 10 reaction conduits).

In an alternative embodiment, a heat transfer fluid is flowed in one or more cooling conduits (e.g., heat exchange conduits) adjacent to one or more reaction conduits (e.g., process flow conduits). The flow of heat transfer fluid may be cross flow, counter-flow or co-flow. Each of these conduits may isolate the flow to provide indirect heat transfer between the respective streams.

The exchange of heat produced during the selective hydrogenation of the alkyne-containing feed stock to the alkene-containing product to the heat transfer fluid is through a material, such as a ceramic or metal, having a relatively high thermal conductivity so that the heat can be most effectively removed from the alkene-containing product. More effective heat removal means result in the hydrogenation catalyst being subjected to less heat over time, thereby reducing deactivation of the catalyst due to heat degradation.

The exchange of heat to the heat transfer fluid is through a heat exchange material. For example, the heat exchange material can be the material through which heat is exchanged in a heater exchanger, whether internal or external to the hydrogenation converter, as described above. In one embodiment, the heat exchange material has a thermal conductivity of at least 10 W/m-C at operating conditions. Preferably, the material has a thermal conductivity of at least 50 Watts per meter-Celsius (W/m-C), more preferably a thermal conductivity of at least 100 W/m-C. Examples of such materials include a variety of metals, such as those comprised of at least one compound selected from the group consisting of aluminum, beryllium, brass, copper, gold, iron, nickel, cobalt, chromium, lead, silver, carbon, tungsten, tin and zinc.

The hydrogenation catalyst can be formed on an inner wall of the conduit, or it can be deposited into the conduit using a variety techniques. Any suitable method for loading, attaching or sufficiently adhering the catalyst onto the conduit can be used. For example, catalyst can be formed onto an inner wall of the conduit by techniques, such as wash coating, sol-gel processing, or chemical vapor deposition. In addition, relatively large particles of catalyst, such as powders, spray dried particulates, or smaller pellets can be transferred or slid into the conduit. Catalyst can also be placed or formed in a partly assembled conduit. For example, catalyst can be deposited on a sheet before the sheet is formed into a conduit.

Catalyst particle size can vary depending upon the cross sectional area of the conduit in which the catalyst is contained. For example, larger catalyst particles can be used in conduits having larger cross sectional area. In general, the hydrogenation catalyst particles have an average diameter of ≤500 micrometers (μm), preferably ≤200 μm, and more preferably ≤100 μm. Catalyst particles can be loaded into the converter by any suitable means. For example, a magnetic field can be applied to a conduit and catalyst particles loaded under the influence of the magnetic field. As another example, catalyst particles can be loaded into a conduit that has an electric potential. In an alternative embodiment, the catalyst particles are charged or are sufficiently polarizable such that the particles need not be charged. In yet another alternative embodiment, catalyst particles can be prepared in a solid form and coated or loaded into a conduit, such as by using sonication. In addition, or alternatively, to loading particles, magnetic or electric fields can be used to orient catalyst particles within conduit. For example, particles can be loaded (either with or without a magnetic or electric field) into a conduit and subsequently oriented under a magnetic or electric field.

The flow of the feed stream through at least one conduit is preferably at a flow rate in which pressure drop in the flow path through the at least one conduit is lessened. In one embodiment, the feed stream is flowed through the at least on conduit at a pressure drop of ≤10 psi (69 kPa) per meter of conduit.

Hydrogen may also be added, along with the alkyne in the feed stream. Preferably, the feed stream includes hydrogen at a $H_2/C_2H_2$ molar feed ratio of from 0.5 to 50; alternatively from 1.0 to 20.

The reaction can be in the vapor phase or in the liquid phase. In the vapor phase, the reaction can be carried out at a gas hourly space velocity (GHSV) of from 100 to 25,000 hr$^{-1}$; such as from 500 to 15,000 hr$^{-1}$. In the liquid phase, the reaction can be carried out at a liquid hourly space velocity (LHSV) of from 0.5 to 100 hr$^{-1}$, such as from 1 to 25 hr$^{-1}$.

IV. Alkyne Stream Composition

The feed stream that includes the alkyne to be selectively hydrogenated can come from any suitable source. The feed stream should include a sufficient amount of alkyne to produce heat that can be recovered for energy efficiency purposes. Preferably, the feed stream includes alkyne in an amount ≥2 mol %, ≥4 mol %, ≥20 mol %, but is ≤30 mol % or other suitable limit below any auto-detonation limit for a given composition at a operating pressure and temperature. Preferably, the alkyne is acetylene or methyl acetylene, more preferably acetylene. The feed stream can include non-alkyne compounds. Preferably, the feed stream includes ≤98 mol % non-alkyne compounds, alternatively ≤96 mol % non-alkyne compounds, alternatively ≤80 mol % non-alkyne compounds, alternatively ≤70 mol % non-alkyne compounds, the content of the non-alkyne compounds being based on total weight of the feed stream. Regardless, the process should be managed to be within any auto-detonation limits for a given composition at a operating pressure and temperature. In certain embodiment, to manage the ethylene to acetylene mole ratio, the ethylene to acetylene mole ratio of the reactor effluent may be adjusted to have an ethylene to acetylene mole ratio ≤2:1, ≤5:1, ≤10:1, ≤15:1, or ≤20:1 of the acetylene and ethylene in the reactor effluent, which may be managed via recycle, adjusting the pressure for the conversion and the like.

In a preferred embodiment, the feed stream may also contain small levels of carbon oxides, especially carbon monoxide. Depending on the specific catalyst and operating conditions, the addition of carbon monoxide into the feed stream can be used to reduce formation of fully saturated hydrocarbons such as ethane. Carbon oxides are typically used at lower concentrations in the range of 0.1 to 5 mol % based on the feed gas mixture entering the selective hydrogenation unit or other ranges noted above. Higher amounts may also be used for certain embodiments.

V. Production of Alkyne Stream by Pyrolysis

In an embodiment, the feed stream containing the alkyne that is to be selectively hydrogenated is produced as the product of a pyrolysis reaction or by pyrolyzing a hydrocarbon feed to produce alkyne product. In general, pyrolysis is a thermal decomposition process in which hydrocarbon feed is heated, generally in the absence of oxygen, to decompose the hydrocarbon feed into lower molecular weight hydrocarbon molecules.

The hydrocarbon feed used according to the present techniques can comprise any variety of hydrocarbon compounds. As used herein, the "hydrocarbon feed" contains hydrocarbons (C bound to H) and may contain (i) minor components of heteroatoms (<10 wt %) covalently bound to hydrocarbons and (ii) minor components of heteroatoms (<10 wt %) not bound to hydrocarbons (e.g., $H_2O$), wherein these weight percents are based on the weight of the hydrocarbon feed. Reference to "hydrocarbon compounds" or "hydrocarbons in the hydrocarbon feed" means molecules within the hydrocarbon feed that contain at least hydrogen and carbon and, optionally containing heteroatoms such as oxygen, sulfur and nitrogen. Weight percents of hydrogen and carbon, as used to characterize the hydrocarbon feed, are typically provided as a percent of the hydrocarbons in the hydrocarbon feed. Preferably, the hydrocarbon compounds are comprised of at least 75 percent (%) of both carbon and hydrogen, based on total atom content of the hydrocarbon.

The hydrocarbon feed may include, by way of non-limiting examples, one or more of Fischer-Tropsch products, methane, methane containing streams such as coal bed methane, shale gas, biogas, associated gas, natural gas and mixtures or components thereof, steam cracked gas oil and residues, gas oils, heating oil, jet fuel, diesel, kerosene, gasoline, coker naphtha, steam cracked naphtha, catalytically cracked naphtha, hydrocrackate, reformate, raffinate reformate, Fischer-Tropsch liquids, natural gasoline, distillate, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, C4's/residue admixture, naphtha residue admixture, cracked feedstock, coker distillate streams, hydrocarbon streams derived from plant or animal matter and any mixtures thereof.

Particular hydrocarbons useful according to the present techniques are those that can be pyrolyzed to produce a product containing alkenyl containing compounds, alkynyl containing compounds or both. Particularly preferred are hydrocarbon compounds that can be pyrolyzed to produce an effluent containing $\geq 2$ mol %, more preferably $\geq 3$ mol %, and most preferably $\geq 6$ mol % alkynyl containing compounds, based on total moles of pyrolyzed effluent produced form the pyrolysis process. The preferred alkynyl containing product comprises acetylene.

The term "pyrolysis feed" means the composition, which may be a mixture, subjected to pyrolysis. In one embodiment, the pyrolysis feed is derived from a hydrocarbon feed (e.g., by separation of a portion from the hydrocarbon feed and/or optional diluents). The diluent may be a composition that is used to control partial pressure in the vapor phase. Preferably, the diluent includes compounds that do not include any significant level of oxygen, because the presence of oxygen tends to produce undesirable levels of carbon oxides in the reactor product at the desired pyrolysis temperatures of the process. A preferred diluent is molecular hydrogen ($H_2$), particularly because hydrogen can also react with undesirable carbon by-products to reduce the formation of coke and tar-like by-products.

The pyrolysis feed is the hydrocarbon stream provided to the pyrolysis reactor (e.g., the stream that enters the pyrolysis reactor) and may contain one or more hydrocarbon feeds as well as a molecular hydrogen ($H_2$) containing feed. The pyrolysis feed may include hydrogen gas ($H_2$) in an amount that provides a preferred ratio of hydrogen gas ($H_2$) moles to the total moles of carbon (C) in the hydrocarbon components of the pyrolysis feed. The ratio of hydrogen to carbon ($H_2/C$) may be from 0.0 or 0.1 to 5.0, such as 0.0, 0.1, 1.0, 2.0, 3.0, 4.0, 5.0, or values in between. Combining the hydrogen content of the hydrogen gas to the hydrogen and carbon contents of the hydrocarbon components of the pyrolysis feed may result in a total atomic ratio of hydrogen (H) to carbon (C) in the pyrolysis feed that is in the range of 0.1 to 20, or in the range of 3 to 15. The weight percent of total hydrogen in the pyrolysis feed may be greater than that in the hydrocarbon feed. For example, the weight percent of total hydrogen in the pyrolysis feed may be from 8 wt % to 54 wt %.

The term "hydrogen content" means atomic hydrogen bound to carbon and/or heteroatoms covalently bound thereto and which excludes molecular hydrogen ($H_2$) in the hydrocarbon feed expressed as a weight percent based on the weight of the hydrocarbons in the hydrocarbon feed. Hydrogen content as applied to pyrolysis feed is expressed as a weight percent of hydrocarbons in the respective feed. As used herein, the expression "low hydrogen content feed" or "low hydrogen content hydrocarbon feed" means a feed with a hydrogen content of ≤about 14 wt %. The hydrogen content of hydrocarbon feeds, reactants and products for present purposes can be measured using any suitable protocol (e.g., ASTM D4808-01 (2006), Standard Test Methods for Hydrogen Content of Light Distillates, Middle Distillates, Gas Oils, and Residua by Low-Resolution Nuclear Magnetic Resonance Spectroscopy or ASTM D5291-10 Standard Test Methods for Instrumental Determination of Carbon, Hydrogen, and Nitrogen in Petroleum Products and Lubricants).

As used herein, the terms "coke" and "soot" may refer to hydrocarbonaceous material that accumulates within the reactor during pyrolysis or to solid-phase hydrocarbonaceous materials that emerge from the reactor with the effluent. The hydrocarbonaceous material that accumulates within the reactor during pyrolysis may also be defined as the fraction of the pyrolysis feed that remains in a reactor and thus does not emerge from the reactor as effluent. The reactor product that does emerge may be referred to as the reactor effluent, which is at least a portion of the reactor product.

VI. Reactor for Producing an Alkyne Stream for Selective Hydrogenation

In certain embodiments, the feed stream containing the alkyne that is to be selectively hydrogenated is produced as the product of a conversion reaction in a reactor or derived from the reactor product or reactor effluent. A reactor refers to equipment used for chemical conversion. As such, several items identified as reactors may be combined to become a single entity that is also identified as a reactor, in that individual and combined entities may be characterized as equipment used for chemical conversion. Different types of reactors may be utilized to perform various reactions, which include a thermal pyrolysis reaction, partial oxidation reaction, indirect combustion reaction, and/or arc reaction.

The partial combustion reaction burns part of the feed to supply the heat to pyrolyze the remaining portion of the feed. The partial combustion reaction includes pyrolysis chemistry (e.g., thermochemical decomposition of feed at elevated temperatures in the absence of oxygen) and combustion chemistry (i.e., exothermic chemical reactions between a fuel and an oxidant), with both chemistries occurring at the same time and with the products of both chemistries being an integral part of the reactor product. An example of this process is German Patent No. 875198 and U.S. Pat. Nos. 3,242,223 and 7,208,647.

The indirect combustion reaction contacts a combustion product with the feed to be cracked in the reactor. As such, this process involves pyrolysis and combustion chemistry, but typically the combustion chemistry may occur at a different time or location and the pyrolysis chemistry, while occurring in the presence of combustion products, proceeds in a largely non-oxidative environment, resulting in the products of the two chemistries being an integral part of the reactor product. Examples of these type of reactors include Great Britain Patent No. 834419, German Patent No. 1270537, and U.S. Pat. Nos. 3,419,632 and 7,208,647.

The arc reaction, which includes plasma arc reactors and electric arc reactors, typically involves only pyrolysis chemistry. Examples of these reactors are described in U.S. Pat. Nos. 1,860,624 and 7,119,240.

In general, a pyrolysis reaction is a thermal decomposition process in which pyrolysis feed is heated, generally in the absence of oxygen, to decompose the hydrocarbons into lower molecular weight hydrocarbon molecules. Pyrolysis typically occurs under pressure and at operating temperatures above 430° C. The term "pyrolysis" has also been applied to the decomposition of hydrocarbon material in the presence of superheated water or steam (hydrous pyrolysis), for example, in the steam cracking of hydrocarbon. That is, the thermal pyrolysis reaction involves heating a solid material (e.g., by combustion) and using the heated solid material to provide heat to crack the feed (e.g., via pyrolysis chemistry alone). In the thermal pyrolysis processes, the combustion products are typically maintained separate from the pyrolysis hydrocarbon products or effluent. This reaction involves various different types of reactors, such as U.S. Pat. Nos. 2,319,679; 2,678,339; 2,692,819; 3,024,094; 3,093,697; 7,138,047 and 7,119,240.

A pyrolysis reactor refers to equipment for converting hydrocarbons by means of at least pyrolysis chemistry. The pyrolysis reactor may include one or more reactors and/or associated equipment and lines. That is, in certain embodiments, the pyrolysis reactor may include at least two reactors coupled in series and in fluid communication with each other, or may include two reactor beds in series within a single reactor. Examples of such reactors include, but are not limited to, regenerative reverse-flow reactors as described in U.S. Patent App. Pub. No. 2007/0191664; and pyrolysis reactors as described in U.S. Pat. No. 7,491,250, U.S. Patent App. Pub. Nos. 2007/0144940 and 2008/0142409. These reactors may include a reactor body, wherein the reactor body forms a reaction region within the reactor body; one or more reactor beds within the reaction region and one or more valve assemblies coupled to the reactor body and in flow communication with the reaction region and configured to control fluid flow of the at least a portion of the hydrocarbon containing feed between a location external to the reactor body and within the reaction region.

Such a pyrolysis reactor involves at least pyrolysis chemistry. Pyrolysis or pyrolysis chemistry involves the conversion of hydrocarbons to unsaturates, such as ethylene and acetylene, which is an endothermic reaction requiring addition of heat. The terms "crack" and "cracking" may be used interchangeably with the terms pyrolyse and pyrolysis. In a pyrolysis reaction, ≥50%, ≥80%, or ≥90%, of this heat is provided by heat transfer via solid surfaces, such as tubulars or bed materials. Any combustion chemistry that occurs within the pyrolysis stream of a pyrolysis reactor provides a minority of the endothermic heat of pyrolysis, such as <50%, <20%, or <10% of the endothermic heat of pyrolysis.

Regenerative reverse-flow reactors may involve multiple steps repeated in sequence to form a cycle for the process (e.g., as part of the hydrocarbon processing mode). That is, the process may include two or more sequential steps, which include a heating step to heat the reaction zone and a pyrolysis step that converts the hydrocarbons into the reactor product. The heating step involves reacting combustion streams, which may include two or more individual feeds that are to be combined to form a combustion reaction or a mixture of the two or more feeds, such as a fuel that does not contain oxidants (e.g., $O_2$) or non-combustible non-volatiles and a combustion oxidant that may include an oxygen or oxygen containing fluid. These reactants may include a first reactant comprising ≥5 wt % oxidant and a second reactant comprising ≥1 wt % fuel. The fuel stream may be a hydrogen-containing composition of hydrogen, hydrocarbon or a mixture thereof. The hydrocarbon can be the same or different from the hydrocarbon used in the feed. Another step can be referred to as the pyrolysis step (e.g., pyrolysis or hydrocarbon conversion mode). These different steps may be performed in sequence to form a cycle, which is then repeated as part of the normal hydrocarbon processing operations. The cycle may be performed continuously, semi-continuously, periodically or even as a batch operation. Accordingly, a cycle includes the time spent in heating step plus time spent in pyrolysis step plus any time needed to switch between steps or for additional steps before the repeat of the sequence. Typical cycle times may be in the range of 1 to 240 seconds, or in the range of 2 to 60 seconds. The heating and pyrolysis steps may have equal durations or may be adjusted to have different durations, and may include additional steps (e.g., sweep or purge steps).

As an example, the steps may involve passing streams over a solid material in fixed orientation (e.g., one or more reactor beds), which utilizes valves to alternate introduction of hydrocarbon and/or combustion streams into the internal portion of the reactor. The solid material may be designed to facilitate the process of heat addition and removal. Checker bricks, tiles and monoliths may be used as the solid materials within the reactor. Such materials form a network of passages that are used by the gases in each step to transit the region containing solid material.

The heating step leaves a profile of temperatures in the solid material, that is, a temperature that varies along the path by which the gases transit the solid material. The shape of that profile depends on many factors, including if and where a heat release (combustion) reaction occurs, the initial temperature distribution, the duration of the heating step, the flow rate and inlet temperature of the gas stream, and the heat capacity and transfer properties of the gas and solid material. On average, the solid material is hottest at the end of the heating step.

The pyrolysis step consumes heat and reduces average solid material temperature. The pyrolysis step changes the profile of temperatures in the solid material, in a way that depends on many factors, including where the heat consumption (pyrolysis) reaction occurs, the initial temperature distribution, the duration of the pyrolysis step, the flow rate and inlet temperature of the gas stream, and the heat capacity and transfer properties of the gas and solid. Fixed-solid regenerative pyrolysis reactors do not operate in the steady state. That is, at any given location, the temperature changes. However, these reactors may be in a periodic steady state, meaning that the same cycling of temperatures occurs over and over as the reactor sequentially repeats the heating and pyrolysis steps.

The heat generated from the heating step may preferably be stored in a reactor bed or other solid material. The heat storing and transferring material may be a ceramic, which may include yttria, zirconia, alumina, and/or other refractory material capable of withstanding temperatures within the pyrolysis reactor.

In the present techniques, the regenerative reverse-flow reactor may operate at peak pyrolysis gas temperatures of ≥1200° C., ≥1700° C., ≥2000° C., preferably ≥1400° C., ≥1500° C., or more preferably ≥1540° C. That is, the peak pyrolysis gas temperature ranges may include temperatures in the range from 1200° C. to 2200° C., from 1450° C. to 1700° C., from 1500° C. to 1675° C., or from 1540° C. to 1650° C.

In some reactions, it may even be still more preferable to expose the pyrolysis stream (e.g., hydrocarbon containing steam) to heat using very short residence times, such as ≤0.1 second, to a temperature in excess of 1600° C. When the pyrolysis feed comprises methane, pyrolysis reactions typically include peak pyrolysis gas temperatures in excess of 1400° C. for the methane to react or convert. An exemplary preferred process may pyrolyze the stream within the reactor, such as at peak pyrolysis gas temperatures of from 1540° C. to 2200° C., and more preferably from 1600° C. to 1800° C. Exemplary residence times preferably may be short, such as ≤0.5 second, ≤0.3 second and preferably ≤about 50 milliseconds or in the range of 0.5 seconds to 0.001 seconds.

In an embodiment, the reactor may include components comprised of yttria. In an embodiment, one or more of the reactor beds include separate conduits for separately channeling flow of feed components or regeneration fluid components (e.g., combustion stream components) through the reactor beds. Preferably, each reactor bed includes separate conduits. The separate flow passages (e.g., channels) in the reactor beds can further comprise flow barriers that effectively function as conduit walls to prevent cross flow or mixing of fluids between passages. Each reactor bed preferably includes multiples, which may preferably be in parallel flow arrangement.

In accord with the an embodiment of the present techniques, the regenerative pyrolysis process tends to produce product gas mixtures with higher concentrations of alkynes, particularly acetylene, as compared to more conventional thermal cracking processes such as steam cracking. This alkyne rich gas mixture is more efficiently upgraded to alkenes, such as ethylene, using the selective hydrogenation techniques. In particular, the process may use one or more microchannel converters in combination with a heat transfer fluid to recover heat generated during the hydrogenation reactions. As noted earlier the hydrogenation process can be carried out directly using the vapor phase pyrolysis product or in the liquid phase where the pyrolysis product gas is dissolved into a liquid carrier or solvent using a suitable gas liquid contacting device. In either case, the microchannel converter configuration is particularly well suited to capture the heat generated during hydrogenation for steam generation.

VII. Examples

FIG. 1 is a simplified diagrammatic illustration 200 of an exemplary process for converting hydrocarbon feed into an alkene product, such as ethylene, in accordance with an embodiment of the present techniques. In this illustration 200, a particular configuration of unit operations (i.e. units) are coupled together to convert a hydrocarbon feed into the alkene product. These units may include a conversion reactor 204, solid removal unit 206, a compressor 208, a product separation unit 210, and an acetylene converter 212, which may be a microchannel converter. The process will now be explained in more detail.

A pyrolysis feed is provided via line 221 to the conversion reactor 204, which may be a thermal pyrolysis reactor. The pyrolysis feed may optionally be adjusted to have a hydrogen content within a predetermined range, as noted above. The conversion reactor 204, as noted above, may include a regenerative reverse flow reactor, partial oxidation reactor, indirect combustion reactor, arc reactor or other suitable reactor. Accordingly, the conversion reactor 204 may have different piping configurations to provide combustion feed (e.g., fuel) and the pyrolysis feed separately, depending on the specific configuration.

The reactor effluent from the conversion reactor 204 is conducted away via line 227 to the solid removal unit 206 and other recovery stage units. The solid removal unit 206 may include water scrubbing, oil scrubbing, cyclone separation, electrostatic separation, filtration, and/or moving bed adsorption. As may be appreciated, each of these systems may be combined together in one or more units to overcome certain limitations within the system. For instance, water scrubbing is effective to remove solid carbon black and other solids, but it limits the recovery of heat in the effluent. Oil scrubbing may be utilized for heat recovery, but it may present problems with fouling and emulsion formation. Cyclone separation may be limited to remove solid carbon, but not other smaller or fine solids. Electrostatic separation may have problems with clogging and short-circuiting due to carbon deposit buildup. Adsorption and filtration are limited to handling small amounts of solids and may be problematic for larger amounts of solids. As a result, one or more of these techniques may be coupled together in series to provide the separation.

The solid-liquid phase of the reactor effluent may be conducted away from solid removal unit 206 as a bottoms product, which may be a bottoms stream, via line 229. The bottoms product may include carbon black, soots, and/or heavy aromatic oils and/or tars. If the bottoms product is "dry," it may be handled via filtration or electrostatic separation; if sticky or wet, it may be better handled via washing (oil or water) or absorption. The bottoms product may be recycled to the conversion reactor or may be used as a fuel (in the reactor or process). The remaining portion of the reactor effluent may be withdrawn from solid removal unit 206 as an overhead stream via line 231 and passed to the compressor 208.

The compressor 208 may receive the vapor product from the solid removal unit 306 and compress the product and provide the compressed product via 233 to the product separation unit 210. The compressor 208 may compress to the vapor product to a pressure from 50 psig to 1000 psig (340 kPa to 6900 kPa); alternatively, from 200 psig to 500 psig (1400 kPa to 3900 kPa), from 100 psig to 500 psig (690 kPa to 3900 kPa), from 100 psig to 600 psig (690 kPa to 4137 kPa); or alternatively, from 200 psig to 440 psig (1400 kPa to 3400 kPa). For other embodiments, the pressure may be adjusted for hydrogen ($H_2$) removal (e.g., pressure swing adsorption, hydrogen membrane and/or cryogenic distillation, electrochemical separation) and acetylene hydrogenation.

Once compressed, different products, such as different light gases or heavier products may be separated from at least a portion of the reactor effluent in the product separation unit 210. The product separation unit 210 may include the different units discussed above along with caustic wash, amine scrubber and/or other treatments, which may also include steps to remove different products (e.g., $CO_2$, $H_2S$ and/or $H_2O$) from the process. For instance, carbon dioxide can be removed by washing the reactor effluent. This step may also include drying to remove entrained water. At least a portion of the reactor effluent may be recovered from the product separation unit 210 as via line 237 and passed to the acetylene converter 212, while the impurities may be withdrawn as products or bottom streams via line 235, which may be further processed for the different impurities.

The acetylene converter 212 receives at least a portion of the reactor effluent (e.g., feed stream comprising acetylene and/or ethylene) from the product separation unit 210. The acetylene converter (A/C) selectively hydrogenates the acetylene to ethylene without significantly hydrogenating the ethylene to ethane. The acetylene converter 212, as noted above, may include a microchannel converter, which is operated as described above.

The acetylene converter 212 may include an optional finishing acetylene converter to convert remaining levels of acetylene to near 100 wt % conversion of the acetylene. This finishing acetylene converter may be in fluid communication with one or more units, such as the acetylene converter 212 or other units downstream of the acetylene converter 212. The acetylene converter 212 may further include a compressor, stream recycle components, desorption unit and/or separation unit.

In one embodiment, a conversion product of ≥50 wt % of ethylene may be conducted away from the acetylene converter 212 to storage or for further processing. In addition, coupled to the acetylene converter 212 may be a purification unit and ethylene polymerization unit (not shown). As an example, the purification unit may include a demethanator tower (to remove $H_2$, $CH_4$, $N_2$ and CO) and a $C_2$ splitter to remove ethane and upgrade ethylene to polymer grade ethylene. The purification unit may also include $C_2$ or $C_3$ refrigeration train, compression and additional distillation towers. The ethylene polymerization unit may be a catalytic reactor, which may include a fluidized particulate catalyst for gas phase processing and/or molecular catalysts dispersed into a liquid solvent for solution processing. The process may involve a catalyst, solvent and the feed stream, as discussed above. Further, a portion of the acetylene in the reactor effluent may optionally be combined with other process steps to form other products, such as vinyl esters, ethylene, benzene, acetaldehyde, propanal, propanol, acrylic acid, and/or the like.

In an alternative embodiment, the conversion reactor 204 may be a partial oxidation reactor. With this type of reactor, additional units may be utilized to remove CO or $CO_2$ from the reactor effluents. Also, catalysts may be selected for acetylene conversion and downstream processing that are not impacted (e.g., poisoned) by CO and $CO_2$.

As may be appreciated, the proposed configuration may be utilized to make the existing process more efficient by recovering heat. For instance, if the acetylene converter 212 is a microchannel converter a heat transfer fluid may be utilized to recover energy (e.g., via heat transfer). As one embodiment, the pyrolysis feed may be passed through the microchannel converter prior to passing through the conversion reactor 204. In this manner, the microchannel converter may utilize the exothermic reactions in the converter to further enhance the process.

In yet another embodiment, a heat transfer fluid may pass through the acetylene converter 212 in the various microchannels and be utilized in a heat exchanger upstream of the conversion reactor 204 to heat the pyrolysis feed or may be utilized to assist with separation of various products from the product separation unit 210. The heat recovery may be utilized even if more than one acetylene converter is configured in parallel, series or a combination configuration as well. If the heat recovered from the acetylene converter unit is utilized to preheat the pyrolysis feed, this reduces the heat required within the conversion reactor 204, which increases the efficiency of the overall process. A further example of such energy efficiency is provided in FIG. 2.

Figure 2:
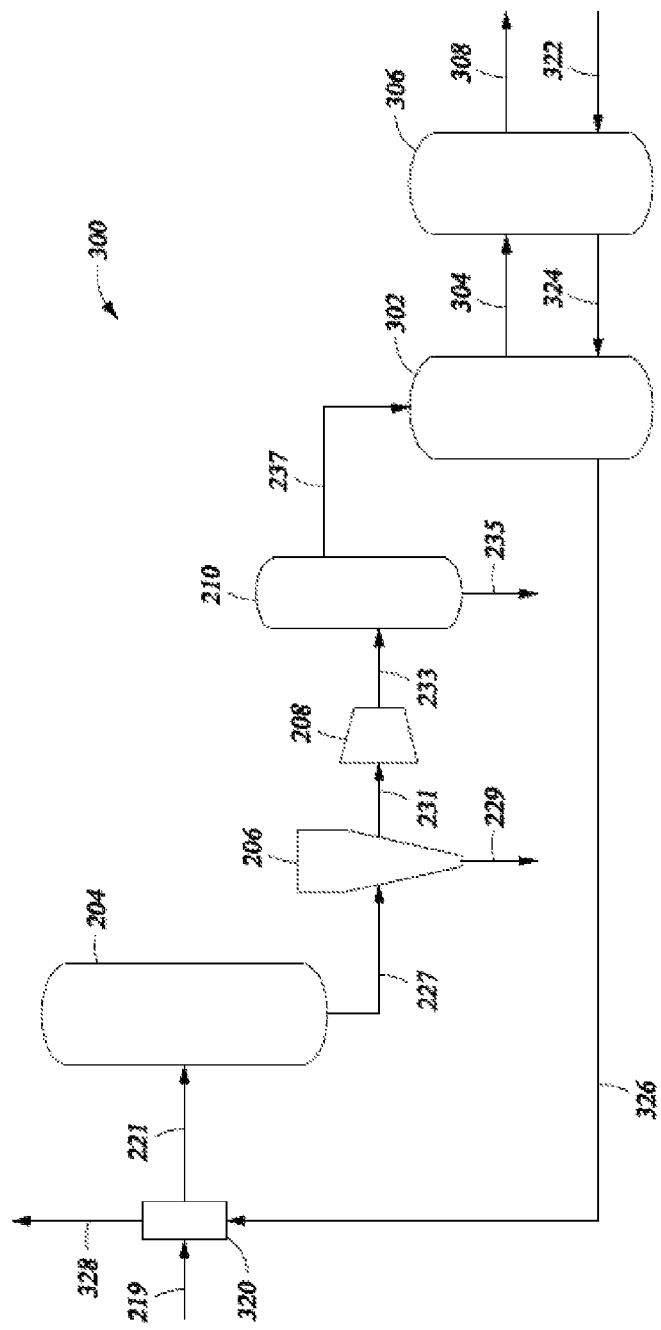
FIG. 2 is a simplified diagrammatic illustration of another exemplary process for convert hydrocarbon feed into conversion products in accordance with an embodiment of the present techniques.

FIG. 2 is a simplified diagrammatic illustration of an exemplary recovery configuration 300 that may be utilized with the present techniques. In this configuration 300, a particular configuration of units is coupled together to convert the feed stream (e.g., a portion of the reactor product or reactor effluent) in an enhanced manner. The configuration 300 includes the units noted above for FIG. 1. In addition, the configuration 300 includes a first acetylene converter 302 and a second acetylene converter 306 coupled in series together. These converters may be utilized to further refine the product from process. Further, the configuration 300 includes a heat exchanger 320 and associated lines 322-328, which are configured to recover heat from the exothermic reactions within the acetylene converters 302 and 306, which is then utilized to preheat the pyrolysis feed prior to the conversion reactor 304. The process will now be explained in more detail.

Similar to the embodiment of FIG. 1, FIG. 2 shows that the reactor effluent from the conversion reactor 204 is passed through various units 206, 208 and 210 and lines 227, 229, 231, 223, 235, and 237. The feed stream derived from the reactor effluent is provided to the first acetylene converter 302 via line 237 and the resulting stream is pass to the second acetylene converter 306 via line 304 for further conversion of the acetylene into ethylene. The application of a second acetylene converter stage may reflect an economic optimization decision for a given plant configuration. For example, if the volumes of acetylene containing gas to be converted are too large for cost effective conversion in a single acetylene convert stage, multiple stages of acetylene converters can be utilized.

Further, to enhance the process, the acetylene converters may be utilized to heat a heat transfer fluid in the multiple stages as part of the process. In this configuration 300, a heat transfer fluid may be provided via line 322 to the second acetylene converter 306 to recovery heat from the reactions in the second acetylene converter 306. Then, the heat transfer fluid may be provided via line 324 to the first acetylene converter 302, and recovery heat from the reactions in the first acetylene converter 302. Once the heat is recovered from these units, the heat transfer fluid may be passed via line 326 to the heat exchanger 320 to transfer heat to the pyrolysis feed in line 220.

Further, as yet another embodiment, the heat transfer fluid may be utilized as a diluent for the conversion reactor in the different configurations above. That is, the heat transfer fluid may be utilized as a diluent for the conversion reactor or may be utilized by another reactor, such as a steam cracking furnace, to function as a diluent for that unit, which may be utilized as part of the same system. In particular, as one embodiment, a steam cracking furnace may be operated in parallel with a conversion reactor with the recovery units being shared between the reactors, such as the acetylene converter being downstream of the conversion reactor and steam cracking reactor. The heat transfer fluid may be heated in the microchannel converter and mixed with the feed to the steam cracking furnace upstream of the radiant section. Optionally, the heat transfer fluid may be preheated in or further heated in the convection section and/or in heat exchangers associated with the steam cracking furnace. Regardless, the heat transfer fluid may be mixed with the feed for the steam cracking furnace as a diluent or as a quench medium.

Figure 3:
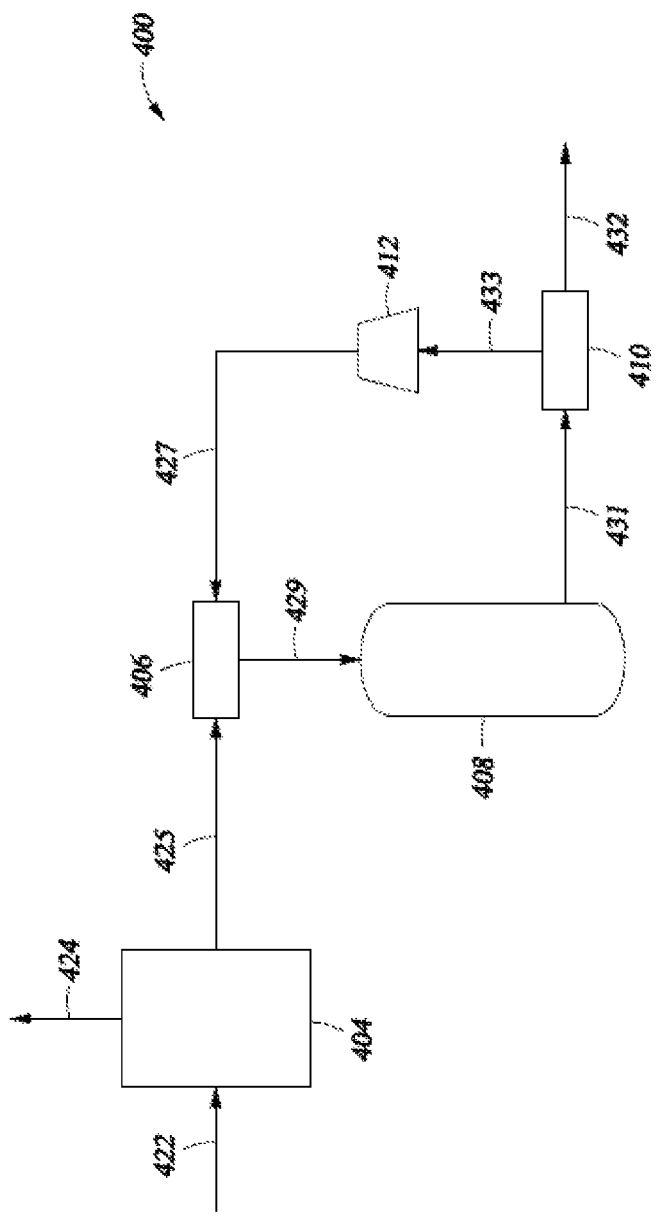
FIG. 3 is a simplified diagrammatic illustration of still yet another exemplary process for convert hydrocarbon feed to conversion products in accordance with an embodiment of the present techniques.

As another variation to the process, the composition of the feed stream may be managed to further enhance the process. For instance, FIG. 3 is a simplified diagrammatic illustration of yet another exemplary recovery configuration 400. In this configuration 400, a particular configuration of units is coupled together to convert a reactor product into a feed stream for the acetylene converter 408. That is, the reactor effluent may be further processed to form a feed stream (e.g., acetylene rich stream) by separating a hydrogen product from the reactor effluent. This configuration 400 includes a hydrogen separation unit 404, a mixer 406, a converter 408, a splitter 410, and a compressor 412. This process may include units similar to those above and may be coupled to the units described above in FIGS. 1 and 2. The process will now be explained in more detail.

A reactor effluent is provided via line 422 to the hydrogen separation unit 404. The reactor effluent, which may be reactor effluent from a conversion reactor (e.g., one or more of the reactors noted above), may include ethylene, hydrogen and acetylene. The hydrogen separation unit 404, which may be one embodiment of the product separation unit 310 of FIG. 3, may include different separation mechanisms to conduct the hydrogen product away from the reactor effluent.

Similar to the discussion above, the hydrogen separation unit 404 may be coupled with other units (not shown) to remove impurities or separate other products. The remaining reactor effluent may be recovered from the hydrogen separation unit 404 via line 425 and provided to a mixing unit 406, while the hydrogen product may be provided via line 424 for further processing. Specifically, the hydrogen product may be used as the hydrogen ($H_2$) containing stream (e.g., diluent feed into a thermal pyrolysis reactor), as a feed stripping medium, as a feed to a hydrotreater, as a fuel for the thermal pyrolysis reactor, or as a product. The hydrogen separation mechanisms may include pressure swing adsorption, membranes and/or cryogenic distillation, and/or electrochemical separation. As a specific embodiment, the separation of a hydrogen product from the reactor effluent may involve providing an acetylene rich product having an acetylene to diluent molar ratio within a preferred range (e.g., below any autodecomposition range for a given pressure and temperature).

The mixing unit 406 may combine the acetylene along with a converter recycle product provided via line 427, which may include ethylene or other suitable products. The mixing unit 406 may include a manifold, sparger or other suitable unit that combines the converter recycle product with the acetylene-rich product. The converter recycle product may be used to control the acetylene level within a preferred range and/or to control the acetylene to ethylene exotherm and selectivity. The mixture is then provided via line 429 to a converter 408, which may be any suitable converter, but is preferably a microchannel converter as noted earlier.

The converter 408 may receive the feed stream (e.g., acetylene-rich product comprising acetylene and ethylene from the reactor) from the mixing unit 406. If the converter 408 is an acetylene converter, it may selectively hydrogenate the acetylene to ethylene without significantly hydrogenating the ethylene to ethane and/or without producing significant levels of green oil. The acetylene converter may operate under process conditions as described above.

The conversion product from the converter 408 may be provided via 431 to a splitter 410. The splitter 410 may separate or divide a portion of the conversion product into a converter recycle product, while the remaining conversion product may be conducted away via line 432 for further processing, as noted above. The splitter 410 may be a joint in the pipes or lines, a flow regulation unit, a manifold or other suitable unit. For instance, the remaining conversion product may be provided to an upgrading unit (not shown).

A converter recycle product may be passed via line 433 to an optional compressor 412. The compressor 412 may be similar to the compressors noted above. The compressor may compress the converter recycle product to have a pressure that matches the inlet pressure. Once compressed the converter recycle product may be provided to the mixer 406 via line 427.

To further enhance the process, the present techniques may include a method to manage the ethylene to acetylene mole ratio for the reactor effluent upstream of the microchannel converter. For instance, in one or more embodiment, the conversion reactor may expose a hydrocarbon feed to a peak pyrolysis gas temperature $\geq 1500.0°$ C. to produce a reactor product. The reactor product or reactor effluent may include $\geq 2$ mol % acetylene, $\geq 4$ mol % acetylene, and/or $\geq 20$ mol %, but may also be $\leq 30$ mol % acetylene. To manage the ethylene to acetylene mole ratio, the ethylene to acetylene mole ratio of the reactor effluent may be adjusted to have an ethylene to acetylene mole ratio $\leq 2:1$, $\leq 5:1$, $\leq 10:1$ or $\leq 20:1$ of the acetylene and ethylene in the reactor effluent, which may be managed via recycle, adjusting the pressure for the conversion and the like. The ethylene to acetylene mole ratio may have a lower limit of $\geq 30:1$, $\geq 25:1$, or $\geq 20:1$ of the acetylene and ethylene in the reactor effluent. Then, the adjusted reactor effluent may be passed to the microchannel converter to produce ethylene from hydrogenation of the adjusted reactor effluent. This adjustment to the ethylene to acetylene mole ratio may be managed by recycling ethylene to the process. That is, in one embodiment, the ethylene produced by the system may be combined with the reactor effluent to adjust this ratio.

Alternatively or in addition to such a recycle, one or more conversion reactors that operate at different temperatures to produce different products may be utilized to provide this functionality. These conversion reactors along with a microchannel converter may be operated as a system that enhances operations because of the recovery of heat along with the management of the products with a lessening of the recycled product (e.g., ethylene). As an example, a first conversion reactor may expose a first hydrocarbon feed to a peak pyrolysis gas temperature $\geq 1500.0°$ C. to produce a first reactor product. This first reactor effluent (e.g., portion of the first reactor product) may include $\geq 2$ mol % acetylene, $\geq 4$ mol % acetylene, or $\geq 20$ mol %. A second conversion reactor may expose a second hydrocarbon feed to a peak pyrolysis gas temperature $\geq 700.0°$ C. to produce a second reactor product. The second reactor effluent (e.g., portion of the second reactor product) may include $\leq 2$ mol % acetylene, $\leq 1$ mol % acetylene or even $\leq 0.5$ mol % acetylene. These reactor effluents may be combined to produce a combined reactor effluent. The combined reactor effluent may also include a recycled stream of additional diluent, such as ethylene from the microchannel converter to further manage the reactor effluents. The microchannel converter may expose the stream to an average hydrogenation reaction temperature greater than or equal to 125° C. to produce a vapor product comprising ethylene.

To monitor this process, various measurement devices may be utilized, which may include various sensors or one or more gas chromatography (GC) devices. These devices may be coupled to various lines within the system to provide the concentrations for the various effluents through the process. For instance, a first GC device may determine a first ethylene to acetylene mole ratio for the first reactor effluent, while a second GC device may determine a second ethylene to acetylene mole ratio for the second reactor effluent. Another GC may be utilized to monitor the concentration of the combined effluents. Then, adjustments may be made based upon one or more of these concentrations. For instance, the adjustments to the amount of recycle within the process may be based on the determined first ethylene to acetylene ratio and the determined second ethylene to acetylene ratio. These mole ratios may be compared to adjust the recycled amount of a diluent or other product to the process.

As additional embodiments, the heat recovered from this system may be utilized to enhance the operation of the system. For instance, the recovered heat from the microchannel converter may be utilized to reduce the amount of reactants (e.g., fuel) provided to one or more of the reactors. Further, the recovered heat in the form of a heat transfer fluid may be utilized as a diluent by combining the heat transfer fluid with the second feed upstream of the second conversion reactor. This may provide heat to the feed to this reactor along with other benefits derived from diluents (e.g., as noted in steam cracking processes). In addition, the recovered heat in the form of a heat transfer fluid may be utilized to heat one or more of the feeds via indirect or direct heat exchange upstream of the respective reactor. Moreover, if the heat transfer fluid is a pressurized vapor, it can be depressurized through an expander turbine device to generate electrical power.

In one or more embodiments, the conversion reactor may be associated with the microchannel converter. For instance, a conversion reactor configured to convert a hydrocarbon containing feed (e.g., pyrolysis feed) into a feed stream containing acetylene, while a microchannel converter may be in fluid communication with the conversion reactor and configured to convert a portion of the acetylene from the feed stream into ethylene. The microchannel converter may include a plurality of process flow conduits and a plurality of heat exchange conduits. One or more of the plurality of process flow conduits may have a catalyst disposed on an interior surface and permit flow of the feed stream through the process flow conduit, while one or more of the plurality of heat exchange conduits are configured to pass a heat exchange fluid through the plurality of heat exchange conduits to recover at least a portion of the heat through heat exchange with the heat transfer fluid. The microchannel converter may be directly coupled to the conversion reactor (e.g., directly coupled to the conversion reactor, which may be a regenerative reverse flow reactor) and/or integrated with the conversion reactor (e.g., the microchannel converter is within the housing of the conversion reactor and/or separated by one or more valves, such as poppet valves, and an associated flow barrier from the reactor beds within the conversion reactor). For example, the conversion reactor may include comprises one or more reactor beds and the microchannel converter is disposed adjacent to at least one of the one or more reactor beds.

To operate, this configuration may include various steps to enhance the process. For instance, the process may include passing an oxidant containing stream and a fuel containing stream to a conversion reactor during a heating step; passing one of the oxidant containing stream and the fuel containing stream through a microchannel converter; reacting the oxidant containing stream and the fuel containing stream to form combustion products and combustion heat within the conversion reactor; removing the combustion products from the conversion reactor; passing the hydrocarbon feed to the conversion reactor; and exposing the hydrocarbon feed to the combustion heat within the conversion reactor to produce the reactor product comprising acetylene, wherein at least a portion of the reactor product is the feed stream. The oxidant may be passed through the microchannel converter to remove coke other byproducts (e.g., regenerate the catalyst), while the fuel may be passed through the microchannel converter to prepare the fuel for combustion.

In addition, the microchannel converter and the conversion reactor may be integrated to further provide additional efficiencies. For instance, one or more conduits may be utilized and configured to transport the heat transfer fluid to the microchannel converter and pass the heat transfer fluid from the microchannel converter to a heat exchanger upstream of the conversion reactor. In this manner, the microchannel converter may be utilized to heat feeds, which may reduce energy consumption for the process. Also, the one or more conduits may be configured to transport the heat transfer fluid to a steam turbine or other system that may be utilized to supply energy to the equipment in the process.

Figure 4:
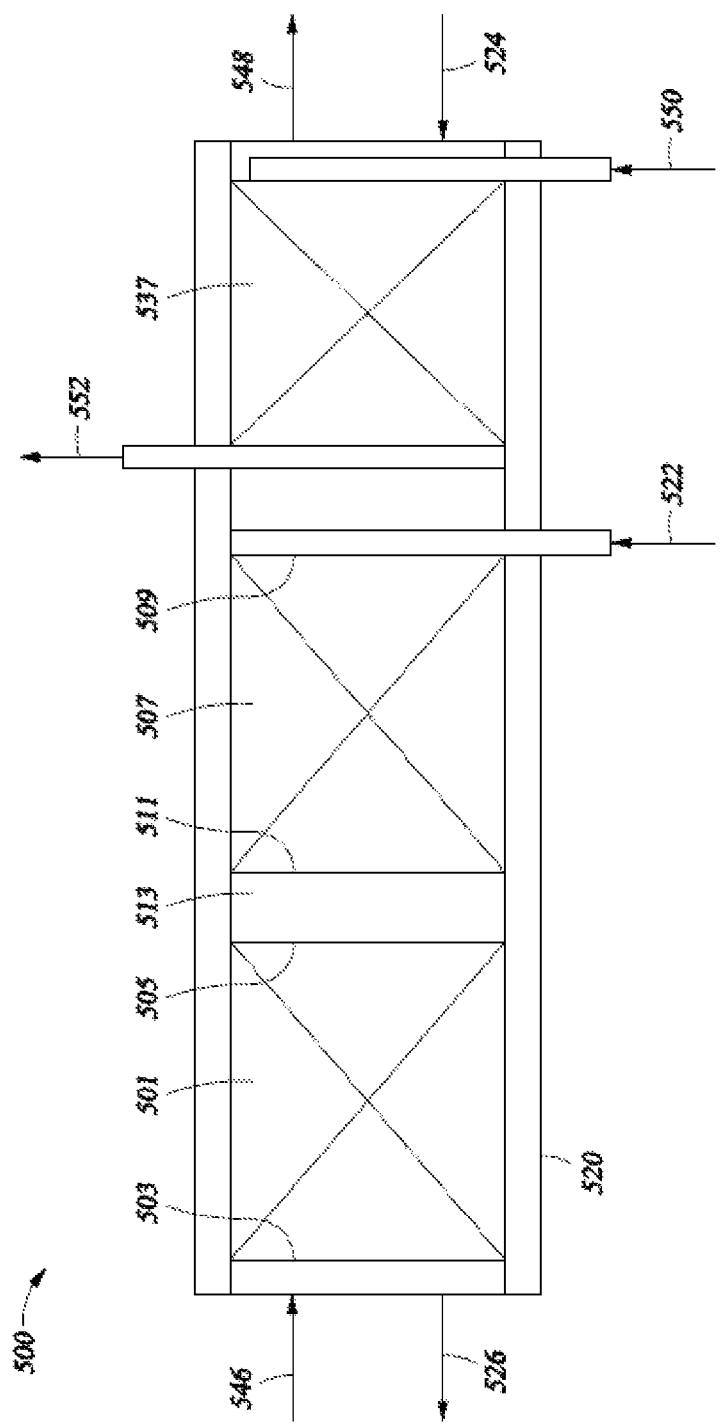
FIG. 4 schematically illustrate a regenerative reverse flow reactor with an integrated microchannel converter in accordance with an embodiment of the present techniques.

In still yet another embodiment, FIG. 4 is a simplified diagrammatic illustration of yet another exemplary configuration 500. In this configuration 500, a regenerative reverse-flow reactor is shown having a microchannel acetylene converter integrated within the reactor. This exemplary embodiment of a regenerative reverse-flow reactor utilizes a two-step asymmetric cycle reaction. The reactor comprises four zones, a first ("recuperator") zone 507, a mixing zone 513, and a second ("reaction") zone 501 and an acetylene conversion zone 537 (e.g., microchannel converter). Zones 501 and 507 each comprise at least one reactor bed, which includes material that is effective in storing and transferring heat. The acetylene conversion zone 537 may include a reactor bed that is a microchannel acetylene converter (e.g., a variation of the configuration noted above). Each of the zones may be surrounded by an insulation component 520. The reactor bed may comprise bedding or packing material, such as glass or ceramic beads or spheres, metal beads or spheres, ceramic (including, e.g., alumina, silica, yttria, zirconia, etc., and mixtures thereof) or metal honeycomb materials, ceramic tubes, extruded monoliths, catalysts, etc. Honeycomb monoliths include, e.g., extruded porous structures such as those that are used for automotive catalytic converters, etc. The term "honeycomb" means a cross-sectional shape that includes multiple flow paths or conduits through the extruded monolith, but the use of this term is not meant to limit the monolith's structure or shape to any particular topology. In embodiments where a honeycomb monolith is used, the honeycomb monolith is believed to enable low pressure loss transference, while providing contact time and heat transfer. The first and second reactors can be, e.g., the same as those described in U.S. Patent App. Pub. No. 2007/0191664.

At the beginning of the pyrolysis step, the reaction zone 501 is at an elevated temperature and the recuperator zone 507 is at a lower temperature than the reaction zone 501. A pyrolysis feed is introduced via a conduit 546, into a first end 503 of the reaction zone 501.

The pyrolysis stream abstracts heat from the reaction zone 501 and is reacted, optionally with a catalyst, to produce the desired pyrolysis reaction. As this step proceeds, a temperature profile is created based on the heat transfer properties of the system, the profile having, e.g., an approximately Gaussian shape. An edge of the temperature profile moves across the reaction zone 501 as the pyrolysis step proceeds.

The reactor product derived from the pyrolysis feed by the pyrolysis exits the reaction zone 501 through a second end 505 at an elevated temperature and passes through the recuperator zone 507, entering through a first end 511 and exiting at a second end 509. The recuperator zone 507 is initially at a lower temperature than the reaction zone 501. As the stream passes through the recuperator zone 507, it is cooled to a temperature subsisting proximate to the second end 509 of zone 507. The temperature at that location can be, e.g., approximately the same temperature as that of the fuel or oxidant introduced at that location during the heating step of the cycle.

A primarily vapor-phase portion of the reactor product is passed through an acetylene conversion zone 537 before being conducted away from the reactor via conduit 548, with another portion of the reactor product optionally remaining in one or more of zones 501, 507, 513, 537, e.g., as a deposit, such as a coke deposit. As the stream passes through the acetylene conversion zone 537, it reacts with the catalyst to convert a portion of the stream (e.g., $C_2$ unsaturates, such as acetylene) into other products (e.g., ethylene). The temperature at that location can be, e.g., approximately the same temperature as that of the fuel or oxidant introduced at that location during the heating step of the cycle.

Within the acetylene conversion zone 537, the reactions to convert a portion of the hydrocarbon containing stream into a reactor product may involve exothermic reactions. Accordingly, a heat transfer fluid may be, optionally, provided via line 550 and may pass through separate conduits (e.g., passages) in the microchannel converter (e.g., microchannel bed) to transfer heat from the exothermic reactions within the acetylene conversion zone 537. The heat transfer fluid may then be conducted away from the reactor via line 552. The resulting heat transfer fluid may be utilized for various processes, such as a diluent, to heat the fuel, oxidant, and/or pyrolysis feed, or other suitable purposes, as noted above.

The heating step entails transferring heat from (i) the mixing zone 513 and optionally (ii) from recuperator zone 507 to the reaction zone 501, to thermally regenerate the reaction zone for subsequent pyrolysis step(s). A combustion reaction is produced by mixing combustion reactants, which may include an oxidant (e.g., oxidant containing stream) and a fuel (e.g., a fuel containing stream). The combustion reaction is performed proximate to combustion zone 513 by mixing and distributing fuel and oxidant. Fuel is conducted to recuperator zone 507 via conduit 522, and oxidant is conducted via conduit 524. The oxidant (e.g., oxidant containing stream) may be passed through the acetylene converter zone 537 to burn off or decoke carbon and green oils remaining on the catalyst or within the acetylene converter zone 537. Optionally, one or more distribution means (not shown) can be utilized for conducting fuel into at least one fuel passage and/or another distribution means can be utilized for conducting oxidant into at least one oxidant passage. The fuel passage(s) and oxidant passage(s) being located within recuperator zone 507. Because the fuel and oxidant passages are independent flow paths (e.g., not in fluid communication one with the other) mixing of fuel and oxidant generally does not occur until mixing zone 513. The fuel and oxidant combine proximate to mixing zone 513 to produce the combustion products. The reaction of the fuel and oxidant in the combustion products is exothermic, which leads to movement of the tails of the temperature profile toward reaction zone 501. In other words, the tails of the temperature profile move across reaction zone 501 and recuperator zone 507, which translate the temperature profile in a direction opposite to the direction in which the profile translated during the pyrolysis step.

At least a portion of the heat abstracted from the recuperator zone 507 by the combustion mixture together with at least a portion of the heat derived from the oxidation reaction (and the products thereof) is transferred to the reaction zone 501, thermally regenerating the bed(s) therein. The combustion products, derived from at least in part from the oxidation of at least a portion of the combustion stream's fuel component, is conducted away from the reactor system via conduit 526. The pyrolysis and heating steps can be operated in sequence, e.g., continuously or semi-continuously, with at least a portion of the heat released during the regeneration steps being utilized by the endothermic pyrolysis steps.

In one or more embodiments, reactants (e.g., one of the fuel and oxidant) may be passed through the acetylene converter (e.g., through the acetylene converter 212, 302, 306 and/or 408 or microchannel convert 537) to preheat the respective reactants. That is, the converter may be utilized to heat the one or more of the reactants (separately) prior to being provided to the conversion reactor. In this manner, the reactant may recover heat from the converter, while the reactant may be used to clean the converter or enhance the process. For instance, in one embodiment, the oxidant may be passed through the acetylene converter (e.g., microchannel converter), which may be utilized to heat the oxidant. In addition, the oxidant may react with coke within the converter to produce additional heat, which may further heat the remaining oxidant stream. This heat recovered from the converter may reduce the amount of feeds utilized by the conversion reactor, which increases the efficiency of the process. In addition, the oxidation of coke may be beneficial by regenerating the catalyst within the converter (e.g., removing the coke and other byproducts that may hinder the acetylene conversion).

In another embodiment, the fuel may be passed through the acetylene converter to heat the fuel prior to passing to the conversion reactor. If a portion of the fuel reacts exothermically in the converter, the heat may be recovered from the converter and passed to the reactor bed. This heat recovered from the converter may reduce the amount of feeds utilized by the conversion reactor, which increases the efficiency of the process. In addition, if the fuel comprises hydrogen (e.g., a sufficient amount of hydrogen in the fuel stream), the coke may react with the hydrogen to decoke the catalyst (e.g., regenerate the catalyst within the converter).

The invention is further defined in terms of the following embodiments.

1. A method for selectively hydrogenating an alkyne, comprising:

flowing a feed stream comprising molecular hydrogen and greater than or equal to 2 mol % alkyne based on the total feed stream through at least one conduit containing a hydrogenation catalyst;

contacting the feed stream with the hydrogenation catalyst to produce an alkene-containing product stream at operating conditions sufficient to provide an alkyne to an alkene conversion rate of at least 0.4 moles/hour/cc of hydrogenation catalyst and to produce heat; and recovering at least a portion of the heat through heat exchange with a heat transfer fluid.

2. The method of embodiment 1, wherein the heat is produced at operating conditions sufficient to yield a catalyst heat release rate ≥1.8 MJ/hr/cc of hydrogenation catalyst.

3. The method of any one of embodiments 1 to 2, wherein the feed stream flows through the conduit at a pressure drop of ≤69 kPa per meter of conduit.

4. The method of any one of embodiments 1 to 3, wherein the conduit has a cross sectional area of less than or equal to 50 $mm^2$ 5. The method of any one of embodiments 1 to 4, wherein the conduit is in a microchannel converter.

6. The method of embodiment 5, wherein the recovering comprises:

passing the heat transfer fluid through at least one of a plurality of conduits in the microchannel converter;

heating the heat transfer fluid via indirect heat transfer; and removing the heat transfer fluid from the microchannel converter.

7. The method of embodiment 6, wherein the indirect heat exchange is through a material having a thermal conductivity of ≥10 W/m-C at operating conditions.

8. The method of any one of embodiments 1 to 7, wherein the hydrogenation catalyst is disposed on an inner wall of the conduit.

9. The method of embodiment 8, wherein the conversion of the alkyne to alkene is carried out in the conduit.

10. The method of any one of embodiments 1 to 9, wherein the feed stream is comprised of at least 4 mol % alkyne based on the total feed stream.

11. The method of any one of embodiments 1 to 10, wherein the alkyne is acetylene or methyl acetylene.

12. The method of any one of embodiments 1 to 11, wherein the alkene is ethylene.

13. The method of any one of embodiments 1 to 12, wherein the operating conditions comprise an average hydrogenation reaction temperature in the range of 125° C. to 500° C.

14. The method of any one of embodiments 1 to 13, wherein the operating conditions comprise a pressure in the range of 340 kPa to 4137 kPa.

15. The method of any one of embodiments 1 to 14, wherein the feed stream comprises molecular hydrogen at a $H_2/C_2H_2$ molar feed ratio in the range from 0.5 to 50.

16. The method of any one of embodiments 1 to 15, wherein the hydrogenation catalyst comprises greater than or equal to 2 wt % of a metal selected from Groups 8 to 10 of the Periodic Table based on the total weight of the hydrogenation catalyst.

17. The method of any one of embodiments 1 to 16, wherein the hydrogenation catalyst comprises >0.5 wt % palladium and/or platinum based on the total weight of the hydrogenation catalyst.

18. The method of any one of embodiments 1 to 17, wherein the hydrogenation catalyst comprises >0.01 wt % of one or more promoter elements selected from Groups 1, 2, 11, 12, 13, and 14 of the Periodic Table based on the total weight of the hydrogenation catalyst.

19. The method of any one of embodiments 1 to 18, wherein the feed stream comprises at least 5 mol % alkyne based on the total feed stream.

20. The method of any one of embodiments 1 to 19, wherein the hydrogenation catalyst has an alkyne conversion ≥80% at operating conditions.

21. The method of any one of embodiments 1 to 20, wherein the hydrogenation catalyst has selectivity to alkene ≥50 mol % at operating conditions.

22. The method of any one of embodiments 1 to 21, wherein the method has selectivity to green oil of ≤10 wt % at operating conditions.

23. The method of any one of embodiments 1 to 22, wherein the feed stream contains less than 2 mol % carbon monoxide based on the total feed stream.

24. The method of any one of embodiments 1 to 23, further comprising utilizing the extracted heat to reduce energy consumption in a conversion reactor, wherein the feed stream is derived from effluent of the conversion reactor.

25. The method of any one of embodiments 1 to 23, further comprising utilizing the extracted heat to perform one or more of (i) generating steam from the heat transfer fluid, (ii) converting the heat transfer fluid into energy, (iii) combining the heat transfer fluid with a hydrocarbon containing feed provided to a conversion reactor, wherein the feed stream is derived from effluent from the conversion reactor, and (iv) heating conversion reactor feed via the heat transfer fluid.

26. The method of any one of embodiments 1 to 23, further comprising utilizing the extracted heat to reduce conversion reactor feed utilized in a conversion reactor, wherein the feed stream is derived from effluent from the conversion reactor.

27. The method of embodiment 26, wherein the utilizing the extracted heat comprises one or more of (i) combining the heat transfer fluid with a hydrocarbon containing feed provided to the conversion reactor, and (ii) heating the hydrocarbon containing feed with the heat transfer fluid.

28. The method of any one of embodiments 1 to 24, 26 and 27, wherein the heat transfer fluid is one or more of water and steam.

29. The method of any one of embodiments 1 to 23, further comprising:
passing an oxidant containing stream and a fuel containing stream to a conversion reactor during a heating step;
passing one of the oxidant containing stream and the fuel containing stream through a microchannel converter;
reacting the oxidant containing stream and the fuel containing stream to form combustion products and combustion heat within the conversion reactor;
removing the combustion products from the conversion reactor;
passing a pyrolysis feed to the conversion reactor; and
exposing the pyrolysis feed to the combustion heat within the conversion reactor to produce a reactor product comprising acetylene, wherein the feed stream is derived from at least a portion of the reactor product.

30. The method of embodiment 29, further comprising exposing the pyrolysis feed to a peak pyrolysis gas temperature ≥1500.0° C. within the conversion reactor.

31. The method of any one of embodiments 29 and 30, wherein the conversion reactor is a regenerative reverse flow reactor.

32. A system for processing hydrocarbons to produce ethylene comprising:
a conversion reactor configured to convert a hydrocarbon containing feed into a feed stream containing acetylene;
and a microchannel converter in fluid communication with the conversion reactor and configured to convert a portion of the acetylene from the feed stream into ethylene and having:
a plurality of process flow conduits, wherein at least one of the plurality of process flow conduits have a hydrogenation catalyst disposed on an interior surface and permit flow of the feed stream through the process flow conduit; and
a plurality of heat exchange conduits, wherein the plurality of heat exchange conduits are configured to pass a heat exchange fluid through the plurality of heat exchange conduits to recover at least a portion of the heat through heat exchange with the heat transfer fluid.

33. The system of embodiment 32, wherein the microchannel converter is directly coupled to the conversion reactor.

34. The system of embodiment 32, wherein the microchannel converter is integrated with the conversion reactor.

35. The system of embodiment 34, wherein the conversion reactor comprises one or more reactor beds and the microchannel converter is disposed adjacent to at least one of the one or more reactor beds.

36. The system of embodiment 35, further comprising one or more poppet valves disposed between at least one of the one or more reactor beds and the microchannel converter.

37. The system of any one of embodiments 32 to 36, wherein the at least one of the plurality of process flow conduits has a cross sectional area of less than or equal to 50 mm$^2$ 38. The system of any one of embodiments 32 to 37, wherein the plurality of process flow conduits are formed from a material having a thermal conductivity of ≥10 W/m-C at operating conditions.

39. The system of any one of embodiments 32 to 38, wherein the microchannel converter is configured to operate at a pressure in the range of 340 kPa to 4137 kPa.

40. The system of any one of embodiments 32 to 39, wherein the hydrogenation catalyst comprises greater than or equal to 2 wt % of a metal selected from Groups 8 to 10 of the Periodic Table based on the total weight of the hydrogenation catalyst.

41. The system of any one of embodiments 32 to 40, wherein the hydrogenation catalyst comprises >0.5 wt % palladium or platinum based on the total weight of the hydrogenation catalyst.

42. The system of any one of embodiments 32 to 41, wherein the hydrogenation catalyst comprises >0.01 wt % of one or more promoter elements selected from Groups 1, 2, 11, 12, 13, and 14 of the Periodic Table based on the total weight of the hydrogenation catalyst.

43. The system of any one of embodiments 32 to 41, further comprising one or more conduits configured to transport a heat transfer fluid to the microchannel converter and pass the heat transfer fluid from the microchannel converter to a heat exchanger upstream of the conversion reactor.

44. The system of any one of embodiments 32 to 41, further comprising one or more conduits configured to transport a heat transfer fluid to the microchannel converter and pass the heat transfer fluid from the microchannel converter to a steam turbine.

45. The system of any one of embodiments 32 to 44, wherein the conversion reactor is a regenerative reverse flow reactor and is configured to expose a pyrolysis feed to a peak pyrolysis gas temperature ≥1500.0° C. within the conversion reactor.

46. The system of any one of embodiments 32 to 44, wherein the conversion reactor is a regenerative reverse flow reactor that comprises:
a reactor body, wherein the reactor body forms a reaction region within the reactor body; and
one or more valve assemblies coupled to the reactor body and in flow communication with the reaction region and configured to control fluid flow of the at least a portion of the hydrocarbon containing feed between a location external to the reactor body and within the reaction region.

In one more embodiments, two of more acetylene converters may be utilized in a configuration to provide additional efficiencies to the process. These acetylene converters may individually heat the different reactants (e.g., fuel or oxidant) and/or pyrolysis feed to the conversion reactor. For instance, one reactant may be passed through one acetylene converter, while the second reactant may be passed through the second acetylene converter. In this manner, the reactants may be individually heated upstream of the conversion reactor to enhance the operation of the process.

For a regenerative reverse flow reactor, another advantage of the reverse flow reactor may provide additional advantages. In a reverse flow regenerative reactor, the flow of the pyrolysis feed in the pyrolysis step and the reactants in the heating step further reduce the deactivation of the catalyst. That is, the byproducts formed by flowing the hydrocarbons in the pyrolysis feed through the microchannel converter maybe removed by the flow of the one of reactants. As such, for the shorted cycles, byproducts, such as coke and green oil, may be removed efficiently without the substantial buildup and minimal effect on the activity or selectivity of the catalyst. That is, the catalyst does not degrade due to fouling. Further, the catalyst may be able to maintain operation for longer periods of time without the need for maintenance or offline regenerating activities.

The principles and modes of operation of this invention have been described above with reference to various exemplary and preferred embodiments. As understood by those of skill in the art, the overall invention, as defined by the claims, encompasses other preferred embodiments not specifically enumerated herein.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated.

The invention claimed is:

1. A hydrocarbon pyrolysis process comprising:
a) providing a reverse-flow pyrolysis reactor comprising a heated pyrolysis zone, a mixing zone, a recuperator zone, and an acetylene conversion zone, wherein i) the mixing zone is located between the pyrolysis zone and the recuperator zone, ii) the recuperator zone is located between the mixing zone and the acetylene conversion zone, iii) the acetylene conversion zone has a plurality of process flow conduits, and iv) at least one of the acetylene conversion zone process flow conduits has a hydrogenation catalyst disposed on an interior surface and is open to flow;
b) providing a pyrolysis feed comprising hydrocarbon;
c) providing a fuel and an oxidant;
d) introducing the pyrolysis feed into the pyrolysis zone and pyrolysing the pyrolysis feed in the pyrolysis zone to i) produce a pyrolysis effluent comprising ≥2 mol % acetylene and ii) transfer heat from the pyrolysis zone to the pyrolysis feed and/or the pyrolysis effluent;
e) transferring heat from the pyrolysis effluent to the recuperator zone to produce a cooled pyrolysis effluent;
f) selectively converting in the acetylene conversion zone at least a portion of the cooled pyrolysis effluent's acetylene to ethylene at a conversion rate of at least 0.4 moles/hour/cc of hydrogenation catalyst, wherein at least a portion of the selective conversion is carried out in the process flow conduits of the acetylene conversion zone;
g) conducting away at least a portion of the ethylene;
h) discontinuing a flow of the pyrolysis feed:
i) introducing the oxidant into the acetylene conversion zone and conducting the oxidant through at least a portion of the process flow conduits of the acetylene conversion zone, transferring heat from the acetylene conversion zone to the oxidant to produce a heated oxidant, and removing at least a portion of any coke or foulant in the process flow conduits;
j) conducting the heated oxidant from the acetylene conversion zone through the recuperator zone and transferring heat from the recuperator zone to the heated oxidant to produce a reheated oxidant;
k) combusting the fuel and the reheated oxidant in the mixing zone to produce a combustion effluent;
l) transferring heat from the combustion effluent to the pyrolysis zone in order to reheat the pyrolysis zone;
m) conducting away the combustion effluent; and
n) discontinuing the flow of the oxidant into the acetylene conversion zone.

2. The process of claim 1, further comprising repeating steps d) through n).

3. The process of claim 1, wherein the fuel is conducted through the recuperator zone in at least one fuel passage and the oxidant is conducted through the recuperator zone through at least one oxidant passage, the fuel and oxidant passages being independent flow paths to substantially prevent the mixing of the fuel and the oxidant upstream of the mixing zone, upstream being with respect to flow paths of the fuel and the oxidant.

4. The process of claim 1, wherein the pyrolysis feed and/or the oxidant is conducted through at least one of a plurality of heat exchange conduits adjacent to the process flow conduits in the acetylene conversion zone and heat is indirectly transferred from the acetylene conversion zone to the pyrolysis feed and/or the oxidant, the acetylene conversion zone being configured to substantially prevent fluid communication between the heat exchange conduits and the process flow conduits.

5. A hydrocarbon pyrolysis process comprising:
  a) providing a reverse-flow pyrolysis reactor comprising a heated pyrolysis zone, a mixing zone, a recuperator zone, and an acetylene conversion zone, wherein i) the mixing zone is located between the pyrolysis zone and the recuperator zone, ii) the recuperator zone is located between the mixing zone and the acetylene conversion zone, iii) the acetylene conversion zone has a plurality of process flow conduits, and iv) at least one of the acetylene conversion zone process flow conduits has a hydrogenation catalyst disposed on an interior surface and is open to flow;
  b) providing a pyrolysis feed comprising hydrocarbon;
  c) providing a fuel and an oxidant;
  d) introducing the pyrolysis feed into the pyrolysis zone and pyrolysing the pyrolysis feed in the pyrolysis zone to i) produce a pyrolysis effluent comprising ≥2 mol % acetylene and ii) transfer heat from the pyrolysis zone to the pyrolysis feed and/or the pyrolysis effluent;
  e) transferring heat from the pyrolysis effluent to the recuperator zone to produce a cooled pyrolysis effluent;
  f) selectively converting in the acetylene conversion zone at least a portion of the cooled pyrolysis effluent's acetylene to ethylene at a conversion rate of at least 0.4 moles/hour/cc of hydrogenation catalyst, wherein at least a portion of the selective conversion is carried out in the process flow conduits of the acetylene conversion zone;
  g) conducting away at least a portion of the ethylene;
  h) discontinuing a flow of the pyrolysis feed:
  i) introducing the fuel into the acetylene conversion zone and conducting the fuel through at least a portion of the process flow conduits of the acetylene conversion zone, transferring heat from the acetylene conversion zone to the fuel to produce a heated fuel, and removing at least a portion of any coke or foulant in the process flow conduits;
  j) conducting the heated fuel from the acetylene conversion zone through the recuperator zone and transferring heat from the recuperator zone to the heated fuel to produce a reheated fuel;
  k) combusting the reheated fuel and the oxidant in the mixing zone to produce a combustion effluent;
  l) transferring heat from the combustion effluent to the pyrolysis zone in order to reheat the pyrolysis zone;
  m) conducting away the combustion effluent; and
  n) discontinuing the flow of the fuel into the acetylene conversion zone.

6. The process of claim 5, further comprising repeating steps d) through n).

7. The process of claim 5, wherein the fuel is conducted through the recuperator zone in at least one fuel passage and the oxidant is conducted through the recuperator zone through at least one oxidant passage, the fuel and oxidant passages being independent flow paths to substantially prevent the mixing of the fuel and the oxidant upstream of the mixing zone, upstream being with respect to flow paths of the fuel and the oxidant.

8. The process of claim 5, wherein the pyrolysis feed and/or the fuel is conducted through at least one of a plurality of heat exchange conduits adjacent to the process flow conduits in the acetylene conversion zone and heat is indirectly transferred from the acetylene conversion zone to the pyrolysis feed and/or the fuel, the acetylene conversion zone being configured to substantially prevent fluid communication between the heat exchange conduits and the process flow conduits.

* * * * *